US011091795B2

(12) United States Patent
Desai

(10) Patent No.: US 11,091,795 B2
(45) Date of Patent: Aug. 17, 2021

(54) COMPOSITIONS AND METHODS FOR DIAGNOSING AND TREATING ARRHYTHMIAS

(71) Applicant: Arizona Board of Regents on Behalf of the University of Arizona, Tucson, AZ (US)

(72) Inventor: Ankit Desai, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 224 days.

(21) Appl. No.: 16/317,475

(22) PCT Filed: Jul. 11, 2017

(86) PCT No.: PCT/US2017/041444
§ 371 (c)(1),
(2) Date: Jan. 11, 2019

(87) PCT Pub. No.: WO2018/013509
PCT Pub. Date: Jan. 18, 2018

(65) Prior Publication Data
US 2019/0249232 A1    Aug. 15, 2019

Related U.S. Application Data

(60) Provisional application No. 62/360,649, filed on Jul. 11, 2016.

(51) Int. Cl.
| *C12Q 1/68* | (2018.01) |
| *C12Q 1/6827* | (2018.01) |
| *C12Q 1/6883* | (2018.01) |
| *C12Q 1/6806* | (2018.01) |
| *C12Q 1/6809* | (2018.01) |
| *C12Q 1/6816* | (2018.01) |
| *C12Q 1/6851* | (2018.01) |
| *C12Q 1/6853* | (2018.01) |
| *C12Q 1/6858* | (2018.01) |

(52) U.S. Cl.
CPC ......... *C12Q 1/6827* (2013.01); *C12Q 1/6806* (2013.01); *C12Q 1/6809* (2013.01); *C12Q 1/6816* (2013.01); *C12Q 1/6851* (2013.01); *C12Q 1/6853* (2013.01); *C12Q 1/6858* (2013.01); *C12Q 1/6883* (2013.01); *C12Q 2600/112* (2013.01); *C12Q 2600/156* (2013.01); *G01N 2800/326* (2013.01)

(58) Field of Classification Search
CPC ...... A61K 31/17; A61K 31/706; A61K 38/20; A61K 2039/505; A61K 31/7105; A61K 31/711; A61K 31/713; A61K 39/395; C07K 16/244; C07K 2317/76; C07K 14/54; C12Q 1/6806; C12Q 1/6809; C12Q 1/6816; C12Q 1/6851; C12Q 1/6858; C12Q 1/6876; C12Q 2600/112; C12Q 2600/156; C12Q 1/6825; C12Q 1/6883; C12Q 1/6827; C12Q 1/6853; G01N 33/50; G01N 2333/54; G01N 2800/326

See application file for complete search history.

(56) References Cited

U.S. PATENT DOCUMENTS

| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,283,174 A | 2/1994 | Arnold et al. |
| 5,399,491 A | 3/1995 | Kacian et al. |
| 5,455,166 A | 10/1995 | Walker |
| 5,480,784 A | 1/1996 | Kacian et al. |
| 5,565,332 A | 10/1996 | Hoogenboom et al. |
| 5,585,089 A | 12/1996 | Queen et al. |
| 5,695,934 A | 12/1997 | Brenner |
| 5,705,188 A | 1/1998 | Junichi et al. |
| 5,710,029 A | 1/1998 | Ryder et al. |
| 5,714,330 A | 2/1998 | Brenner et al. |
| 5,750,341 A | 5/1998 | Macevicz |
| 5,814,447 A | 9/1998 | Ishiguro et al. |
| 5,824,518 A | 10/1998 | Kacian et al. |
| 5,824,544 A | 10/1998 | Armentano et al. |
| 5,830,730 A | 11/1998 | German et al. |
| 5,872,154 A | 2/1999 | Wilson et al. |
| 5,885,808 A | 3/1999 | Spooner et al. |
| 5,912,148 A | 6/1999 | Eggerding |

(Continued)

FOREIGN PATENT DOCUMENTS

| EP | 0684315 | 11/1995 |
| WO | WO 97/30731 | 8/1997 |

(Continued)

OTHER PUBLICATIONS

Infnium® HD Assay Super Protocol Guide, Nov. 2015, Illumina, Document # 11322427 v01, pp. 1-10. (Year: 2015).*

Siegbahn, Agneta, et al. "Evaluation of the Effect of Interleukin 18 Associated Genetic Polymorphisms on Risk of Cardiovascular Events in Patients With Acute Coronary Syndrome." (2013): A17262-A17262. (Year: 2013).*

(Continued)

*Primary Examiner* — Jehanne S Sitton
*Assistant Examiner* — Daniel W Nielsen
(74) *Attorney, Agent, or Firm* — Casimir Jones, S.C.; Tanya A. Arenson

(57) ABSTRACT

The present invention relates to compositions and methods for diagnosing and treating arrhythmias. In particular, the present invention provides IL-18 markers and uses thereof.

7 Claims, 12 Drawing Sheets

(56) References Cited

U.S. PATENT DOCUMENTS

| | | |
|---|---|---|
| 5,925,517 A | 7/1999 | Tyagi et al. |
| 5,928,862 A | 7/1999 | Morrison |
| 5,981,225 A | 11/1999 | Kochanek et al. |
| 5,994,106 A | 11/1999 | Kochanek et al. |
| 5,994,128 A | 11/1999 | Fallaux et al. |
| 5,994,132 A | 11/1999 | Chamberlain et al. |
| 6,001,557 A | 12/1999 | Wilson et al. |
| 6,019,978 A | 2/2000 | Ertl et al. |
| 6,033,908 A | 3/2000 | Bout et al. |
| 6,054,297 A | 4/2000 | Carter et al. |
| 6,130,073 A | 10/2000 | Eggerding |
| 6,150,097 A | 11/2000 | Tyagi et al. |
| 6,180,370 B1 | 1/2001 | Queen et al. |
| 6,210,891 B1 | 4/2001 | Nyren et al. |
| 6,258,568 B1 | 7/2001 | Nyren |
| 6,303,305 B1 | 10/2001 | Wittwer et al. |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,329,492 B2 | 2/2008 | Hardin et al. |
| 7,482,120 B2 | 1/2009 | Buzby |
| 7,501,245 B2 | 3/2009 | Quake et al. |
| 8,084,599 B2 | 12/2011 | Rossi et al. |
| 2004/0234523 A1 | 11/2004 | Dinarello et al. |
| 2005/0042638 A1 | 2/2005 | Arnold et al. |
| 2005/0130173 A1 | 6/2005 | Leamon et al. |
| 2006/0046265 A1 | 3/2006 | Becker et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2009/0297517 A1 | 12/2009 | Sims et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2011/0182872 A1 | 7/2011 | Young |
| 2012/0128626 A1 | 5/2012 | Smith |
| 2014/0011863 A1 | 1/2014 | Young |
| 2015/0250808 A1 | 9/2015 | Deretic et al. |

FOREIGN PATENT DOCUMENTS

| | | |
|---|---|---|
| WO | WO 99/02685 | 1/1999 |
| WO | WO 00/09675 | 2/2000 |
| WO | WO 00/12738 | 3/2000 |
| WO | WO 00/018957 | 4/2000 |
| WO | WO 2006/084132 | 8/2006 |

OTHER PUBLICATIONS

Ss781160189, NCBI, NLM, rs80008802, May 30, 2013. (Year: 2013).*

Ss780971031, NCBI, NLM, rs12796114, May 30, 2013. (Year: 2013).*

Ss781154316, NCBI, NLM, rs5744285, May 30, 2013. (Year: 2013).*

McKie et al. 2016, "A study to investigate the efficacy and safety of an anti-interleukin-18 monoclonal antibody in the treatment of type 2 diabetes mellitus",PLoS ONE 11(3): pp. 1-2. (Year: 2016).*

U.S. Appl. No. 11/671,956, filed Oct. 25, 2007, Volkov et al.

U.S. Appl. No. 11/781,166, filed Oct. 2, 2008, Battulga et al.

Adessi, et al. Solid phase DNA amplification: characterisation of primer attachment and amplification mechanisms. Nucleic Acids Res. Oct. 15, 2000;28(20):E87.

Almeida, C.B., et al. Hydroxyurea and a cGMP-amplifying agent have immediate benefits on acute vaso-occlusive events in sickle cell disease mice. Blood. Oct. 4, 2012;120(14):2879-88.

Al-Zaiti, et al., Electrocardiographic predictors of sudden and non-sudden cardiac death in patients with ischemic cardiomyopathy. Heart Lung. Nov.-Dec. 2014;43(6):527-33.

Anderson, MLM, Young BD (1985) Quantitative filter hybridization. In: Hames BD, Higgins SJ (eds) Nucleic acid hybridisation: a practical approach. Oxford UK: IRL Press, pp. 73-111.

Astier, et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Behr, E.R., et al. Role of invasive EP testing in the evaluation and management of hypertrophic cardiomyopathy. Card Electrophysiol Rev. Dec. 2002;6(4):482-6.

Bennett, et al., Toward the 1,000 dollars human genome. Pharmacogenomics. Jun. 2005;6(4):373-82.

Blankenberg, et al., Interleukin-18 and the risk of coronary heart disease in European men: the Prospective Epidemiological Study of Myocardial Infarction (PRIME). Circulation. Nov. 18, 2003;108(20):2453-9.

Blankenberg, et al., Interleukin-18 is a strong predictor of cardiovascular death in stable and unstable angina. Circulation. Jul. 2, 2002;106(1):24-30.

Brenner, et al. Gene expression analysis by massively parallel signature sequencing (MPSS) on microbead arrays. Nat Biotechnol. Jun. 2000;18(6):630-4.

Brunner, M., et al. Mechanisms of cardiac arrhythmias and sudden death in transgenic rabbits with long QT syndrome. J Clin Invest. Jun. 2008;118(6):2246-59.

Calloe, K., et al. Differential effects of the transient outward K(+) current activator NS5806 in the canine left ventricle. J Mol Cell Cardiol. Jan. 2010;48(1):191-200.

Cerqueira, BA, et al. Increased concentrations of IL-18 and uric acid in sickle cell anemia: contribution of hemolysis, endothelial activation and the inflammasome. Cytokine. Nov. 2011;56(2):471-6.

Chacko, P, et al. Myocardial infarction in sickle cell disease: use of translational imaging to diagnose an under-recognized problem. J Cardiovasc Transl Res. Oct. 2013;6(5):752-61.

Charache, S., et al. Effect of hydroxyurea on the frequency of painful crises in sickle cell anemia. Investigators of the Multicenter Study of Hydroxyurea in Sickle Cell Anemia. N Engl J Med. May 18, 1995;332(20):1317-22.

Darbari, DS, et al. Circumstances of death in adult sickle cell disease patients. Am J Hematol. Nov. 2006;81(11):858-63.

Datta V, Hayden R. 2011. In Vitro Nucleic Acid Amplification Techniques, p. 33-61. In Persing D, Tenover F, Tang Y, Nolte F, Hayden R, van Belkum A (ed), Molecular Microbiology. ASM Press, Washington, DC. doi: 10.1128/9781555816834.ch3.

Desai, AA, et al. A Novel Molecular Signature for Elevated Tricuspid Regurgitation Velocity in Sickle Cell Disease. Am J Respir Crit Care Med. Aug. 15, 2002;186(4):359-68.

Desai, AA, et al. Mechanistic insights and characterization of sickle cell disease-associated cardiomyopathy. Circ Cardiovasc Imaging. May 2014;7(3):430-437.

Desimone, J., et al. Maintenance of elevated fetal hemoglobin levels by decitabine during dose interval treatment of sickle cell anemia. Blood. Jun. 1, 2002;99(11):3905-8.

Duarte, et al. Genome-wide analysis identifies IL-18 as a novel gene associated with diastolic function in sickle cell disease. PLoS One. Sep. 16, 2016;11(9):e0163013.

Erbay, E. Fine-tuning inflammasome activity with a small molecule or ketogenic diet, Science Translational Medicine. Mar. 18, 2015, vol. 7, No. 279; p. 1, 1st and 2nd paragraphs; DOI: 10.1126/scitranslmed.aaa9862.

Fiset, C., et al. A rapidly activating sustained K+ current modulates repolarization and excitation-contraction coupling in adult mouse ventricle. J Physiol. Nov. 1, 1997;504 ( Pt 3):557-63.

(56) References Cited

OTHER PUBLICATIONS

Fitzhugh, et al., Cardiopulmonary complications leading to premature deaths in adult patients with sickle cell disease. Am J Hematol. Jan. 2010;85(1):36-40.
Fontaine, JM, et al. Clinical assessment of the risk for sudden cardiac death in patients with sickle cell anemia. J Natl Med Assoc. Apr. 2008;100(4):360-8.
Gladwin, et al., Cardiovascular abnormalities in sickle cell disease. J Am Coll Cardiol. Mar. 27, 2012;59(13):1123-33.
Graham, JK, et al. Sickle cell lung disease and sudden death: a retrospective/prospective study of 21 autopsy cases and literature review. Am J Forensic Med Pathol. Jun. 2007;28(2):168-72.
Gu, H, et al. The protective role of interleukin-18 binding protein in a murine model of cardiac ischemia/reperfusion injury. Transpl Int. Dec. 2015;28(12):1436-44.
Guatelli, et al., Isothermal, in vitro amplification of nucleic acids by a multienzyme reaction modeled after retroviral replication. Proc Natl Acad Sci U S A. Mar. 1990;87(5):1874-8.
Hamideh, D, et al. Sickle cell disease related mortality in the United States (1999-2009). Pediatr Blood Cancer. Sep. 2013;60(9):1482-6.
Hartford, M, et al. Interleukin-18 as a predictor of future events in patients with acute coronary syndromes. Arteriosclerosis, thrombosis, and vascular biology. Arterioscler Thromb Vasc Biol. Oct. 2010;30(10):2039-46.
Hernesiemi, et al., Interleukin 18 gene promoter polymorphism: a link between hypertension and pre-hospital sudden cardiac death: the Helsinki Sudden Death Study. Eur Heart J. Dec. 2009;30(23):2939-46.
Hernesniemi, et al., Interleukin-18 promoter polymorphism associates with the occurrence of sudden cardiac death among Caucasian males: the Helsinki Sudden Death Study. Atherosclerosis. Feb. 2008;196(2):643-9.
Holloman, KL, et al. Electrocardiogram analysis in adult patients with sickle cell disease. J Natl Med Assoc. Aug. 1987;79(8):809-14.
Indik, et al., Associations of Prolonged QTc in Sickle Cell Disease. PLoS One. Oct. 13, 2016;11(10):e0164526.
Kenigsberg, D.N., et al. Prolongation of the QTc interval is seen uniformly during early transmural ischemia. J Am Coll Cardiol. Mar. 27, 2007;49(12):1299-305.
Kim, et al., Synthetic dsRNA Dicer substrates enhance RNAi potency and efficacy. Nat Biotechnol. Feb. 2005;23(2):222-6.
Kim, S.H., et al. Structural requirements of six naturally occurring isoforms of the IL-18 binding protein to inhibit IL-18. Proc Natl Acad Sci U S A. Feb. 1, 2000;97(3):1190-5.
Koshy, M., et al. 2-deoxy 5-azacytidine and fetal hemoglobin induction in sickle cell anemia. Blood. Oct. 1, 2000;96(7):2379-84.
Kricka, L.J. ed., Nonisotopic Probing, Blotting, and Sequencing, ch. 17. 2d ed. 1995.
Kuroda, J., et al. NADPH oxidase 4 (Nox4) is a major source of oxidative stress in the failing heart. Proc Natl Acad Sci U S A. Aug. 31, 2010;107(35):15565-70.
Kwoh, et al., Transcription-based amplification system and detection of amplified human immunodeficiency virus type 1 with a bead-based sandwich hybridization format. Proc Natl Acad Sci U S A. 1989;86(4):1173-7.
Lebensburger, J.D., et al. Hydroxyurea therapy requires HbF induction for clinical benefit in a sickle cell mouse model. Haematologica. Sep. 2010;95(9):1599-603.
Li, et al., Delayed endosome-dependent CamKII and p38 kinase signaling in cardiomyocytes destabilizes Kv4.3 mRNA. J Mol Cell Cardiol. May 2012;52(5):971-7.
Li, X., et al. Redox control of K+ channel remodeling in rat ventricle. J Mol Cell Cardiol. Mar. 2006;40(3):339-49.
Liem, et al., Prolonged QTc interval in children and young adults with sickle cell disease at steady state. Pediatr Blood Cancer. Jul. 2009;52(7):842-6.
Liu, M., et al., STAT3 regulates MMP3 in heme-induced endothelial cell apoptosis. PLoS One. Aug. 13, 2013;8(8):e71366.
Lizardi, et al., Exponential Amplification of Recombinant-RNA Hybridization Probes. BioTechnol. 1988; 6: 1197-1202.
London, B., et al. Dispersion of repolarization and refractoriness are determinants of arrhythmia phenotype in transgenic mice with long QT. J Physiol. Jan. 1, 2007;578(Pt 1):115-29.
Lundby, A., et al. Effect of the I(to) activator NS5806 on cloned K(V)4 channels depends on the accessory protein KChIP2. Br J Pharmacol. Aug. 2010;160(8):2028-44.
MacLean, et al., Application of 'next-generation' sequencing technologies to microbial genetics. Nat Rev Microbiol. Apr. 2009;7(4):287-96.
Maisel, A, et al. Continuous electrocardiographic monitoring in patients with sickle-cell anemia during pain crisis. Clin Cardiol. Jul. 1983;6(7):339-44.
Maleckar, M.M., et al. NS5806 partially restores action potential duration but fails to ameliorate calcium transient dysfunction in a computational model of canine heart failure. Europace. Nov. 2014;16 Suppl 4:iv46-iv55.
Manci, EA, et al. Causes of death in sickle cell disease: an autopsy study. Br J Haematol. Oct. 2003;123(2):359-65.
Manci, et al., Pathology of Berkeley sickle cell mice: similarities and differences with human sickle cell disease. Blood. 2006;107(4):1651-8.
Margulies, et al., Genome sequencing in microfabricated high-density picolitre reactors. Nature. Sep. 15, 2005;437(7057):376-80.
Mitra, et al., Fluorescent in situ sequencing on polymerase colonies. Anal Biochem. Sep. 1, 2003;320(1):55-65.
Morozova, et al. Applications of next-generation sequencing technologies in functional genomics. Genomics. Nov. 2008;92(5):255-64.
Mueller, BU, et al. Prolonged QT interval in pediatric sickle cell disease. Pediatr Blood Cancer. Nov. 2006;47(6):831-3.
Mullis, et al., Specific synthesis of DNA in vitro via a polymerase-catalyzed chain reaction. Methods Enzymol. 1987;155:335-50.
Murakawa, et al., Direct detection of HIV-1 RNA from AIDS and ARC patient samples. DNA. May 1988;7(4):287-95.
Nguyen, T.P., et al., Arrhythmogenic consequences of myofibroblast-myocyte coupling. Cardiovasc Res. Feb. 1, 2012;93(2):242-51.
Niss, O, et al., Cardiomyopathy With Restrictive Physiology in Sickle Cell Disease. JACC Cardiovasc Imaging. Mar. 2016;9(3):243-52.
O'Brien, L.C., et al., Interleukin-18 as a therapeutic target in acute myocardial infarction and heart failure. Mol Med. Jun. 12, 2014;20:221-9.
Pennisi, E. Genomics. Semiconductors inspire new sequencing technologies. Science. Mar. 5, 2010;327(5970):1190.
Pesse, B., et al., Peroxynitrite activates ERK via Raf-1 and MEK, independently from EGF receptor and p21Ras in H9C2 cardiomyocytes. J Mol Cell Cardiol. May 2005;38(5):765-75.
Platis, A, et al., The effect of daily administration of IL-18 on cardiac structure and function. Perfusion. Jul. 2008;23(4):237-42.
Pomerantz, BJ, et al., Inhibition of caspase 1 reduces human myocardial ischemic dysfunction via inhibition of IL-18 and IL-1beta. Proc Natl Acad Sci U S A. Feb. 27, 2001;98(5):2871-6.
Remme, CA, et al., Late sodium current inhibition in acquired and inherited ventricular (dys)function and arrhythmias. Cardiovasc Drugs Ther. Feb. 2013;27(1):91-101.
Reshef, D. et al., MINE: Maximal Information-based Nonparametric Exploration. Retrieved from http://www.exploredata.net/Downloads/P-Value-Tables, (51).
Rivers, A., et al., RN-1, a potent and selective lysine-specific demethylase 1 inhibitor, increases gamma-globin expression, F reticulocytes, and F cells in a sickle cell disease mouse model. Exp Hematol. Jul. 2015;43(7):546-53.e1-3.
Roden, D.M. Taking the "idio" out of "idiosyncratic": predicting torsades de pointes. Pacing Clin Electrophysiol. May 1998;21(5):1029-34.
Rose, et al., Functional polarity is introduced by Dicer processing of short substrate RNAs. Nucleic Acids Res. Jul. 26, 2005;33(13):4140-56.
Rutledge, CA, et al., c-Src kinase inhibition reduces arrhythmia inducibility and connexin43 dysregulation after myocardial infarction. J Am Coll Cardiol. Mar. 11, 2014;63(9):928-34.

(56) References Cited

OTHER PUBLICATIONS

Sara, JD, et al., Coronary microvascular dysfunction is associated with baseline QTc prolongation amongst patients with chest pain and nonobstructive coronary artery disease. J Electrocardiol. Jan.-Feb. 2016;49(1):87-93.

Schwartz, PJ, et al., QT interval prolongation as predictor of sudden death in patients with myocardial infarction. Circulation. Jun. 1978;57(6):1074-7.

Shendure, et al., Accurate multiplex polony sequencing of an evolved bacterial genome. Science. Sep. 9, 2005;309(5741):1728-32.

Steinberg, M.H., et al., Effect of hydroxyurea on mortality and morbidity in adult sickle cell anemia: risks and benefits up to 9 years of treatment. JAMA. Apr. 2, 2003;289(13):1645-51.

Steinberg, M.H., et al., Fetal hemoglobin in sickle cell anemia: determinants of response to hydroxyurea. Multicenter Study of Hydroxyurea. Blood. Feb. 1, 1997;89(3):1078-88.

Su, F. et al. Bcl-2-associated athanogene 3 protects the heart from ischemia/reperfusion injury, JCI Insight. Nov. 17, 2016; 1(19): e90931.

Sun, X., et al., The NAMPT Promoter Is Regulated by Mechanical Stress, Signal Transducer and Activator of Transcription 5, and Acute Respiratory Distress Syndrome-Associated Genetic Variants. Am J Respir Cell Mol Biol. Nov. 2014;51(5):660-7.

Terse, P., et al., Subchronic oral toxicity study of decitabine in combination with tetrahydrouridine in CD-1 mice. Int J Toxicol. Mar.-Apr. 2014; 33(2):75-85.

Upadhya, B, et al., Prolongation of QTc intervals and risk of death among patients with sickle cell disease. Eur J Haematol. Aug. 2013;91(2):170-8.

Vinchi, et al., Hemopexin therapy improves cardiovascular function by preventing heme-induced endothelial toxicity in mouse models of hemolytic diseases. Circulation. 2013;127(12):1317-29.

Voelkerding, et al., Next-generation sequencing: from basic research to diagnostics. Clin Chem. Apr. 2009;55(4):641-58.

Wadgaonkar, R., et al., Endothelial cell myosin light chain kinase (MLCK) regulates TNFalpha-induced NFkappaB activity. J Cell Biochem. Feb. 1, 2005;94(2):351-64.

Walker, G. et al., Isothermal in vitro amplification of DNA by a restriction enzyme/DNA polymerase system. Proc Natl Acad Sci U S A. Jan. 1, 1992;89(1):392-6.

Wang, M, et al., Interleukin 18 in the heart. Shock. Jul. 2008;30(1):3-10.

Weiss, R., Hot prospect for new gene amplifier. Science. Nov. 29, 1991;254(5036):1292-3.

Xie, Y., et al., Effects of fibroblast-myocyte coupling on cardiac conduction and vulnerability to reentry: A computational study. Heart Rhythm. Nov. 2009;6(11):1641-9.

Xing, SS, et al., Overexpression of interleukin-18 aggravates cardiac fibrosis and diastolic dysfunction in fructose-fed rats. Mol Med. Nov.-Dec. 2010;16(11-12):465-70.

Yang, A.S., et al., Comment on "Chromosomal instability and tumors promoted by DNA hypomethylation" and "Induction of tumors in nice by genomic hypomethylation". Science. Nov. 14, 2003;302(5648):1153; author reply 1153.

Yang, KC, et al., Mechanisms of sudden cardiac death: oxidants and metabolism. Circ Res. Jun. 5, 2015;116(12):1937-55.

Ye, S.Q., et al., Pre-B-cell colony-enhancing factor as a potential novel biomarker in acute lung injury. Am J Respir Crit Care Med. Feb. 15, 2005;171(4):361-70.

Yu, Q., et al., IL-18 induction of osteopontin mediates cardiac fibrosis and diastolic dysfunction in mice. Am J Physiol Heart Circ Physiol. Jul. 2009;297(1):H76-85.

Zhang, L.Q., et al., Interactions between PBEF and oxidative stress proteins—a potential new mechanism underlying PBEF in the pathogenesis of acute lung injury. FEBS Lett. Jun. 11, 2008;582(13):1802-8.

Zhang, X, et al. Hypoxic response contributes to altered gene expression and precapillary pulmonary hypertension in patients with sickle cell disease. Circulation. Apr. 22, 2014;129(16):1650-8.

Zhou, C., et al., AUF1 is upregulated by angiotensin II to destabilize cardiac Kv4.3 channel mRNA. J Mol Cell Cardiol. Dec. 2008;45(6):832-8.

Zhou, C., et al., Delayed endosome-dependent CamKII and p38 kinase signaling in cardiomyocytes destabilizes Kv4.3 mRNA. J Mol Cell Cardiol. May 2012;52(5):971-7.

Zhou, et al., Angiotensin II and stretch activate NADPH oxidase to destabilize cardiac Kv4.3 channel mRNA. Circ Res. Apr. 28, 2006;98(8):1040-7.

Ziv, O., et al., A novel, minimally invasive, segmental myocardial infarction with a clear healed infarct borderzone in rabbits. Am J Physiol Heart Circ Physiol. Jun. 1, 2012;302(11):H2321-30.

* cited by examiner

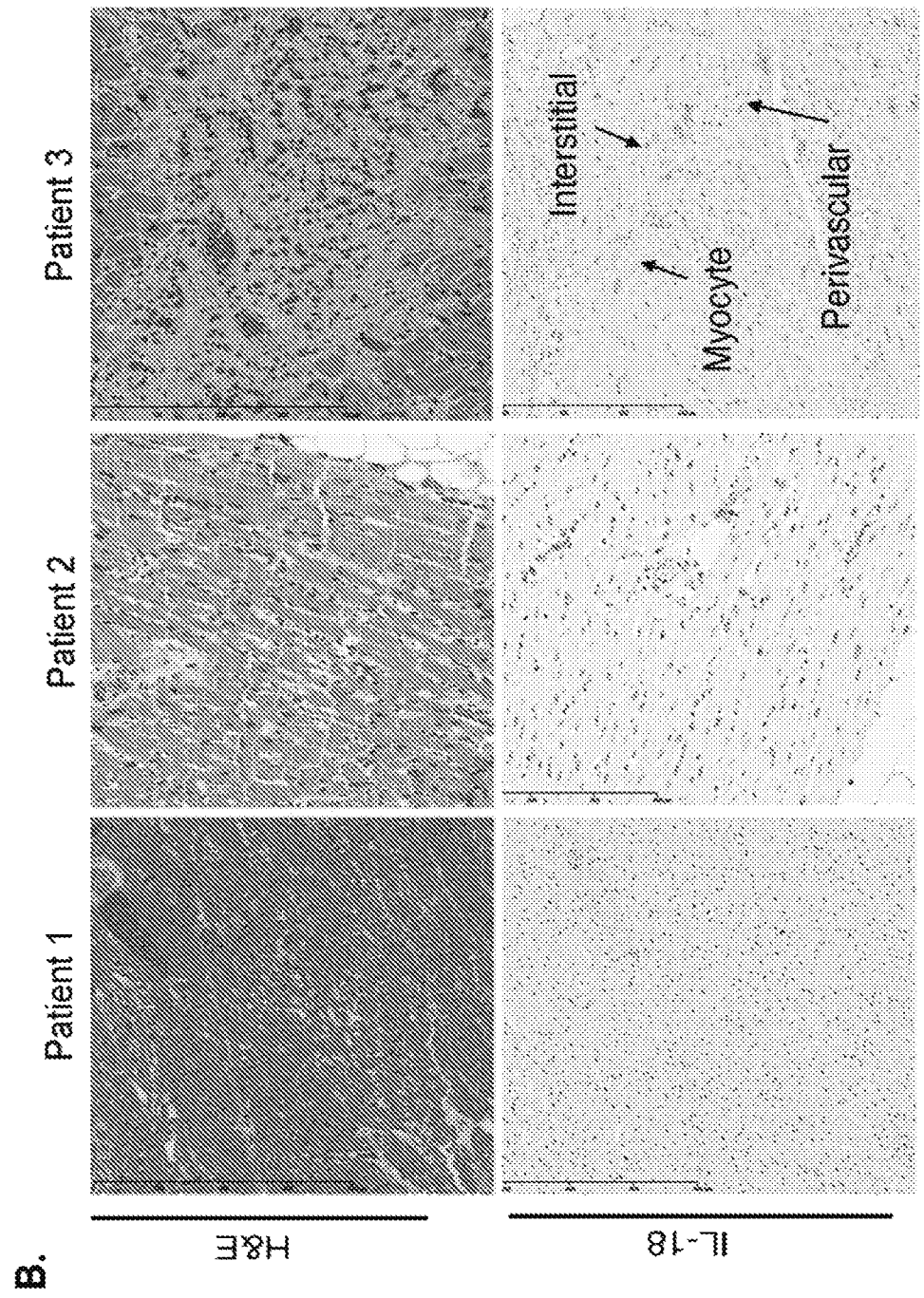

*p<0.05, **p<0.01, Compared with Ctrl group.
†p<0.05, Compared with Sickle group.

COMPOSITIONS AND METHODS FOR DIAGNOSING AND TREATING ARRHYTHMIAS

CROSS-REFERENCE TO RELATED APPLICATIONS

The present application is a Section 371 U.S. national stage entry of International Patent Application No. PCT/US2017/041444. International Filing Date Jul. 11. 2017 which claims priority to U.S. Provisional Patent Application Ser. No. 62/360,649, filed Jul. 11, 2016, the disclosure of which are herein incorporated by reference in their entireties.

FIELD OF THE INVENTION

The present invention relates to compositions and methods for diagnosing and treating arrhythmias. In particular, the present invention provides IL-18 markers and uses thereof.

BACKGROUND OF THE INVENTION

Sickle cell disease is a monogenic disorder, with molecular origins associated with a beta globin mutation. Since the disorder's initial discovery of molecular origins, significant progress has been made in extending the lifespan of patients with the widespread use of newborn screening, hydroxyurea, and vaccinations (Hamideh and Alvarez, *Pediatr Blood Cancer.* 2013; 60(9):1482-6). Despite these advancements over the past 60 years, the prognosis remains poor and the average lifespan for patients is only in the 40s-50s (Hamideh et al., supra). Based on autopsy studies, the top causes of premature death in these patients are acute chest syndrome, pulmonary hypertension, and sudden death (Hamideh et al., supra; Fitzhugh et al., *Am JHematol.* 2010; 85(1):36-40; Graham et al., *Am J Forensic Med Pathol.* 2007; 28(2):168-72; Darbari et al., *Am J Hematol.* 2006; 81(11):858-63; Manci et al., *Br J Haematol.* 2003; 123(2):359-65). While respiratory failure from acute chest syndrome and right heart failure from pulmonary hypertension are well established consequences leading to death, the concept of arrhythmic sudden death in sickle cell disease has not been well characterized.

Case reports have highlighted several predisposing ECG parameters which imply the risk of developing fatal arrhythmias and sudden cardiac death in sickle cell disease. Abnormal QT dispersion and microvolt T wave tests, as well as prolonged QT have been described in sickle cell disease patients (Holloman et al., *J Natl Med Assoc.* 1987; 79(8): 809-14; Liem et al., *Pediatr Blood Cancer.* 2009; 52(7):842-6; Mueller et al., *Pediatr Blood Cancer.* 2006; 47(6):831-3; Upadhya et al., *Eur J Haematol.* 2013; 91(2):170; Fontaine et al., *J Natl Med Assoc.* 2008; 100(4):360-8). Case reports and series have also described the detection of ventricular arrhythmias in sickle cell disease patients (Maisel et al., *Clin Cardiol.* 1983; 6(7):339-44; Chacko et al., *J Cardiovasc Transl Res.* 2013; 6(5):752-61). Recently, associations between an increased QTc interval with hemolysis, free heme, and mortality have been reported in a large sickle cell disease patient cohort followed over 5 years. Nevertheless, it is not clear how hemolysis may be associated mechanistically with abnormal QTc and arrhythmic risk.

In the general population, dilated and hypertrophic cardiomyopathy with myocardial fibrosis has an increased risk of developing ventricular arrhythmias and sudden cardiac death. Similarly, a significant subset of sickle cell patients have also been reported to have myocardial fibrosis and significant diastolic dysfunction, the latter also associated with mortality in sickle cell disease (Desai et al., *Circ Cardiovasc Imaging.* 2014; 7(3):430-7; Niss et al., *JACC Cardiovasc Imaging.* 2016; 9(3):243-52). Therefore, sickle cell and other potential hemolytic anemia states may behave similar to hypertrophic cardiomyopathy given the similar risk profile for the development of fatal arrhythmias.

Additional methods for diagnosing and treating potential ventricular and non-ventricular arrhythmias are therefore urgently needed.

SUMMARY OF THE INVENTION

The present invention relates to compositions and methods for diagnosing and treating arrhythmias. In particular, the present invention provides IL-18 markers and uses thereof. Experiments described herein demonstrated that sickle cell patients with evidence of myocardial fibrosis demonstrated greater IL18 expression. Patients with higher IL18 gene expression levels also exhibited increased QTc intervals and overall mortality. A novel SNP within IL-18, rs5744285, was associated with both QTc and IL-18 expression levels. Similar to sickle cell patients, sickle mice demonstrated increased cardiac fibrosis and prolonged action potential duration (APD) associated with higher VT inducibility. Administration of exogenous IL-18 acutely ex vivo to hearts resulted in increased triggered activity and VTs while inhibition of IL-18 resulted in reduced cardiac NFκB expression, fibrosis, and dysfunction in sickle mice.

IL-18 was associated with prolonged QTc, myocardial fibrosis, and mortality in sickle cell patients, and prolonged APD associated with heightened VT susceptibility in sickle mice. Inhibition of IL-18 improves cardiac function, in part, via NFκB. Inflammatory cytokines contribute to the development of sickle cardiomyopathy and inducible VT.

Accordingly, provided herein, in some embodiments, the present invention provides a method of detecting the presence of a variant IL-18 gene in a sample from a subject, comprising: a) contacting a sample from a subject with a nucleic acid reagent that specifically hybridizes to a variant IL-18 gene but not with a non-variant IL-18 gene, wherein the variant IL-18 gene comprises CT at rs5744285; and b) detecting a hybrid resulting thereof. In some embodiments, the method further comprises the step of detecting one or more additional variants in said IL-18 gene, wherein the variants are selected from, for example, C at rs11214107; a haplotype of T at rs5744285 and C at rs11214107; a haplotype of C at for rs11214107 and A at rs12796114; or a haplotype of G at rs5744285 and C at rs80008802. The present invention isn't limited to particular sample types. For example, in some embodiments, the sample is a cardiac or blood sample. In some embodiments, the subject has sickle cell disease, sickle cell trait, hemolytic anemia, or increased levels of heme or IL-18 in circulation, blood samples, or tissue. The present invention isn't limited to particular reagents. For example, in some embodiments, the nucleic acid reagent is selected from, for example, one or more nucleic acid probes that specifically bind to said variant IL-18 gene, one or more amplification primers that specifically bind to said variant IL-18 gene, or one or more sequencing primers that specifically bind to said variant IL-18 gene. In some embodiments, the nucleic acid reagent is detectably labelled. The present invention isn't limited to particular detection methods. Examples include, but are not limited to, a hybridization assay, a sequencing assay, or a amplification assay. In some embodiments, IL-18 expression is increased in the sample relative to a sample lacking the variant IL-18 gene. In some embodiments, the variant IL-18 gene comprises one or more variant nucleic acids in the promoter region (e.g., those described herein).

Further embodiments provide a method of predicting an outcome in a subject selected from, for example, increased likelihood of developing ventricular arrhythmia, prolonged QTc time, myocardial fibrosis, or diastoilic dysfunction, comprising: a) detecting the presence of a variant IL-18 gene in a sample from the subject, wherein the variant IL-18 gene comprises CT at rs5744285; and b) providing an indication of increased likelihood of developing ventricular arrhythmia, prolonged QTc time, myocardial fibrosis, or diastoilic dysfunction when the variant IL-18 gene is present.

Certain embodiments provide a method of predicting an outcome in a subject selected from, for example, increased likelihood of developing ventricular arrhythmia, prolonged QTc time, myocardial fibrosis, sudden death or diastoilic dysfunction, comprising: a) detecting the presence of increased expression of an IL-18 gene in a sample from the subject; and b) providing an indication of increased likelihood of developing ventricular arrhythmia, prolonged QTc time, myocardial fibrosis, sudden death, or diastoilic dysfunction when increased expression of the IL-18 gene is present.

Additional embodiments provide a method of treating or preventing cardiac dysfunction, comprising: a) detecting the presence of a variant IL-18 gene in a sample from a subject, wherein the variant IL-18 gene comprises CT at rs5744285; and administering anti-IL-18 treatment when the variant IL-18 gene is present. The present invention is not limited to particular anti-IL-18 agents. Examples include, for example, a nucleic acid, an antibody, or a small molecule. In some embodiments, the antibody is interleukin 18 binding protein (IL18BP) or IL-18ab. In some embodiments, the small molecule is hydroxyurea or decitabine.

Yet other embodiments provide a method of preventing or treating ventricular arrhythmia, comprising: administering an anti-IL-18 agent to a subject diagnosed or at risk for ventricular arrhythmia.

Still other embodiments provide the use of an anti-IL-18 agent in the preparation of a medicament for treatment or prevention of ventricular arrhythmia.

Certain embodiments provide a composition, kit, or system, comprising: a nucleic acid reagent that specifically hybridizes to a variant IL-18 gene but not with a non-variant IL-18 gene, wherein the variant IL-18 gene comprises CT at rs5744285.

Additional embodiments are described herein.

DEFINITIONS

Figure 1:
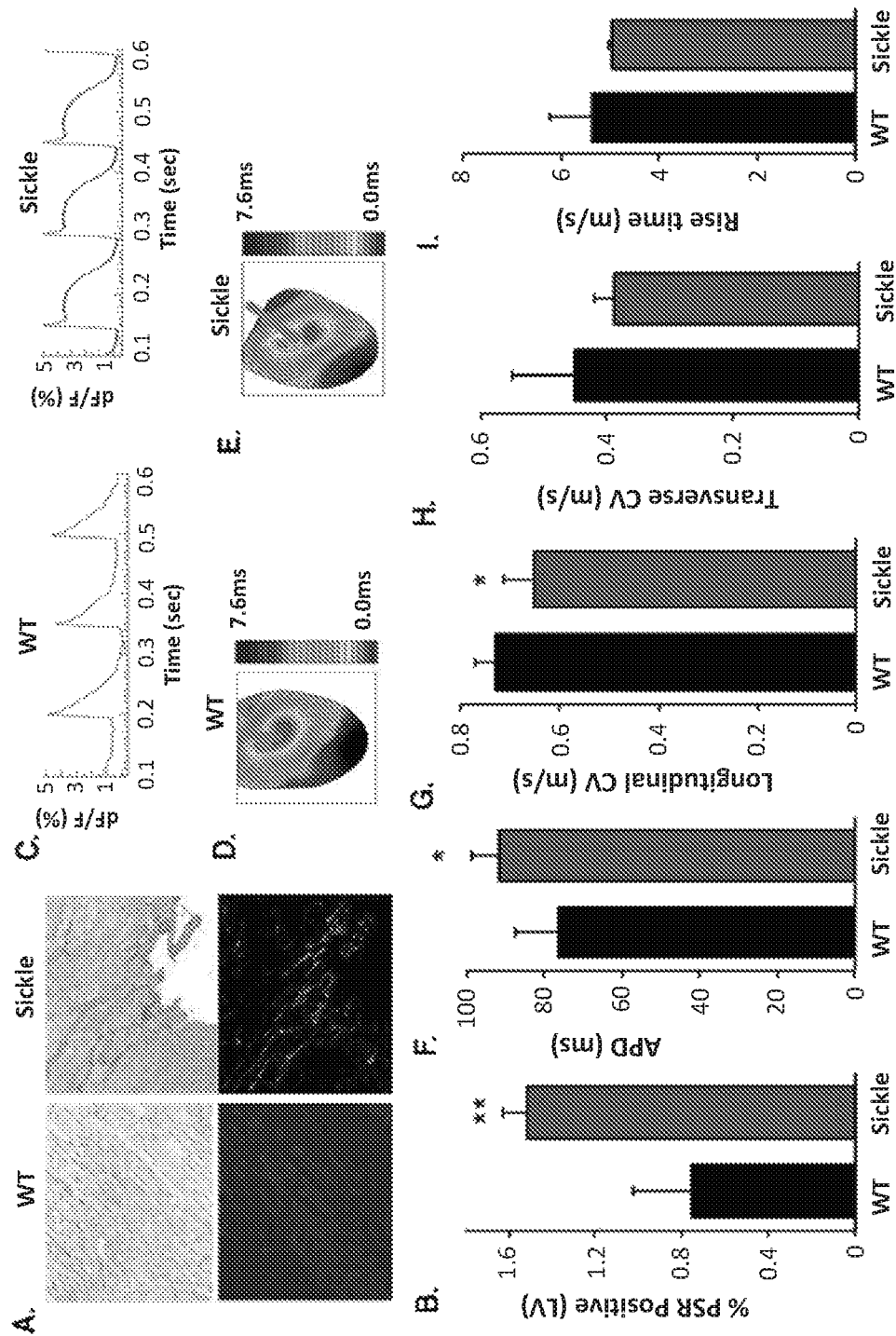
FIG. 1A-I shows myocardial characteristics of sickle cell mice. A. Representative histological examination reveals more myocardial fibrosis in sickle vs WT mice as evidenced by Picrosirius Red (PR) staining. B. Bar graphs demonstrate significantly more fibrosis as measured by % PR staining in LV tissue (n=3/group). C. Action potential traces from control (left) and sickle cell heart (right) at basic cycle length pacing of 150 ms. D. Activation map from the left ventricular center pacing from a WT mouse heart. E. Activation map from a sickle cell mouse heart. The grey bar indicates a stimulation electrode location. F. APD from LV free wall in ms; APDCTR=76.0±11.5, APDSCH=91.5±7.0, *P=0.05, n=5 hearts for each. G. Longitudinal CV (m/s); CVL, CTR=0.73±0.04, CVL,SCH=0.65±0.06, *P=0.049, n=5 hearts for each. H. Transverse CV (m/s); CVT, CTR=0.45±0.11, CVT,SCH=0.39±0.03, P=0.24, n=5 hearts for each. I. Rise Time (ms); RTCTR=5.4±0.04, RTSCH=5.0±0.10, P=0.33, n=5 hearts for each.

To facilitate understanding of the invention, a number of terms are defined below.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous."

The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency or an oligonucleotide and/or mRNA based microarray. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Furthermore, when used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity).

With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the IL-18 gene).

As used herein, the term "detection assay" refers to an assay for detecting the presence or absence of variant nucleic acid sequences (e.g., polymorphism or mutations) in a given allele of a particular gene (e.g., the IL-18 gene).

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding IL-18 includes, by way of example, such nucleic acid in cells ordinarily expressing IL-18 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample. For example, IL-18 antibodies are purified by removal of contaminating non-immunoglobulin proteins; they are also purified by the removal of immunoglobulin that does not bind IL-18. The removal of non-immunoglobulin proteins and/or the removal of immunoglobulins that do not bind IL-18 results in an increase in the percent of IL-18-reactive immunoglobulins in the sample. In another example, recombinant IL-18 polypeptides are expressed in bacterial host cells and the polypeptides are purified by the removal of host cell proteins; the percent of recombinant IL-18 polypeptides is thereby increased in the sample.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the IL-18 mRNA-specific signal observed on Northern blots). The amount of mRNA present in the band corresponding in size to the correctly spliced IL-18 transgene RNA is quantified; other minor species of RNA which hybridize to the transgene probe are not considered in the quantification of the expression of the transgenic mRNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

Sickle cell cardiomyopathy is associated with increased LV mass, myocardial fibrosis, diastolic dysfunction with preserved cardiac output, and prolonged QTc in patients (Desai et al., Circ Cardiovasc Imaging. 2014; 7(3):430-7; Niss et al., JACC Cardiovasc Imaging. 2016; 9(3):243-52; Gladwin et al., J Am Coll Cardiol. 2012; 59(13):1123-33; Manci et al., Blood. 2006; 107(4):1651-8; Vinchi et al., Circulation. 2013; 127(12):1317-29), and APD in mice, predisposing preclinical sickle mice to inducible ventricular tachyarrhythmias and patients to mortality. Since prolonged QTc is associated with an increased risk of mortality (Upadhya et al., supra) in patients, the findings of inducible polymorphic VT in sickle mice, for the first time, links arrhythmic pathology to poor outcomes. Sickle cell mice hearts are characterized by increased myocardial action potential duration and delayed depolarization, decreased conduction velocities, decreased myocardial KCND2 and KCND3 expression levels. This pro-arrhythmogenic phenotype was exacerbated by exogenous IL-18 administration in sickle mice. Furthermore, sickle cell disease patients with higher IL-18 expression (PBMC-derived and protein) also demonstrated an increased prevalence of myocardial fibrosis (cardiac MRI and histology), longer QTc intervals and worse outcomes while inhibition of IL-18 resulted in reduced myocardial inflammation as evidenced by NFκB expression levels, fibrosis and improved diastolic function.

While pacing-induced VT during an electrophysiology (EP) study in parallel conditions such as hypertrophic cardiomyopathy has shown mixed predictive and prognostic value (Behr et al., Card Electrophysiol Rev. 2002; 6(4):482-6), the current observation in sickle cell mice may, nonetheless, still hold several implications on the vulnerability of sickle cardiomyopathy to spontaneous VT or VT induced by hemolytic anemia-specific stress. First, given that murine sickle cardiomyopathy is characterized by three conventional VT risk factors including fibrosis, prolonged APD, and diastolic dysfunction-similar to a subset of patients with sickle cell disease, they represent a potentially high risk arrhythmic vulnerable cohort. Additionally, while a common cause of VT is myocardial scarring from a previous myocardial infarction, polymorphic VT (torsade de pointes), as seen in sickle cell mice, can result from prolonged ventricular repolarization (Al-Zaiti et al., Heart Lung. 2014; 43(6): 527-33; Kenigsberg et al., Journal of the American College of Cardiology. 2007; 49(12):1299-305; Remme and Wilde Cardiovasc Drugs Ther. 2013; 27(1):91-101; Sara et al., J Electrocardiol. 2016; 49(1):87-93; Schwartz and Wolf, Circulation. 1978; 57(6):1074-7). Prolonged QTc is known to be associated with hemolysis in humans with sickle cell disease (Liem et al., supra; Indik et al., supra) and sickle mice have prolonged APD. Therefore, the current data support the potential vulnerability of sickle cell patients and mice to fatal arrhythmias upon exposure to acute hemolysis, especially when coupled with IL18 SNPs that may predispose to higher IL-18 expression. This is further supported by observations of IL-18-induced VT in sickle mice where circulating IL-18 levels in patients are associated with greater indices of hemolysis (Cerqueira et al., Cytokine. 2011; 56(2):471-6).

Figure 5:
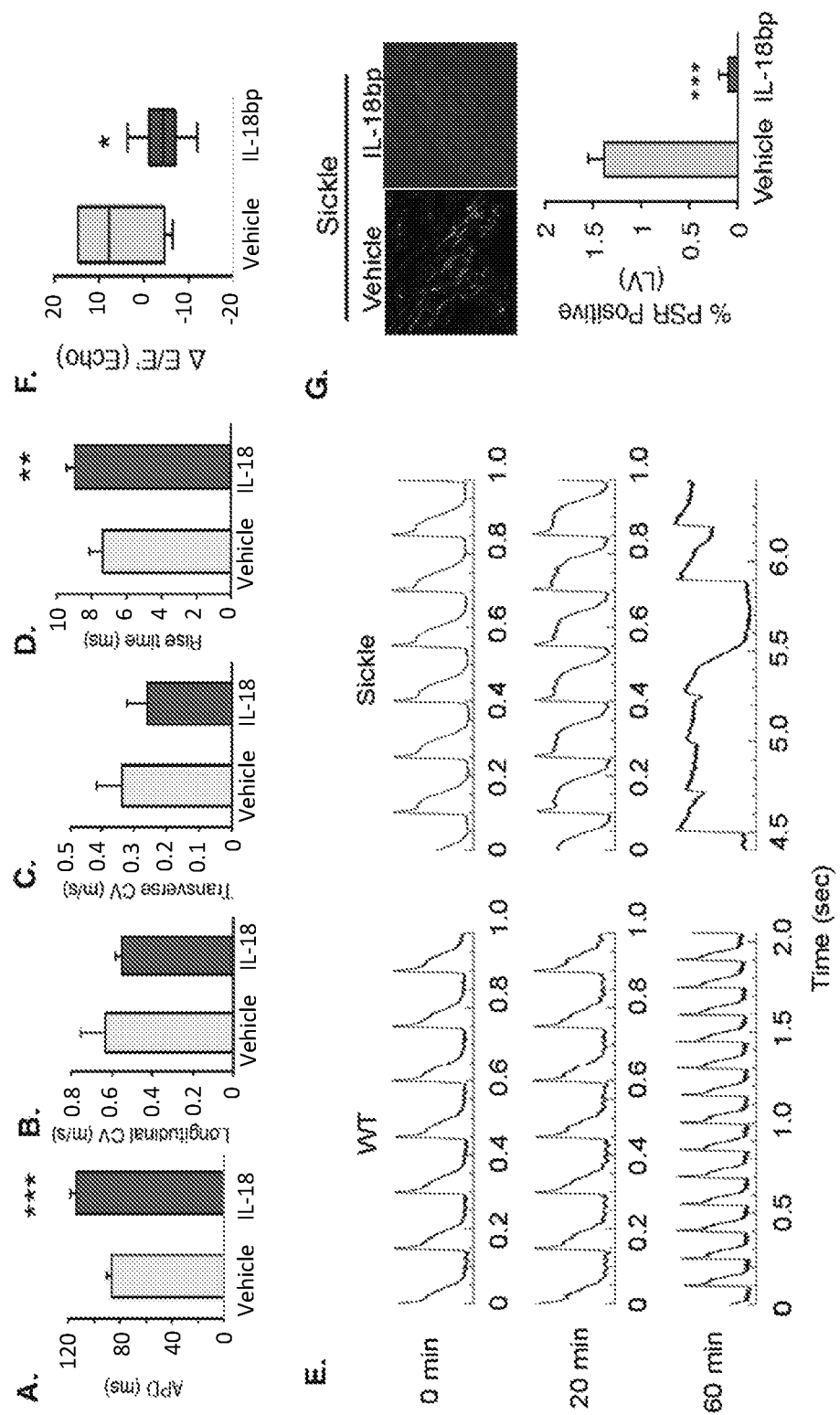
FIG. 5A-G show IL-18 induced PVCs and VTs in sickle cell mice. A. APD prolongation under IL-18 perfusion (20 ng/ml), *p<0.0001 B. and C. Trends in slowing transverse (P=0.078) and longitudinal (P=0.16) CVs with IL-18 perfusion, D. Increased rise time with IL-18 perfusion (P=0.0079). E. ECG tracing after IL-18 perfusion over one hour. F. Echocardiogram data demonstrate improved diastolic function (change in E/E', or LV filling pressures, on echocardiography) with chronic inhibition of IL-18 in sickle mice (*P=0.04). G. As evidenced by Picrosirius Red staining, myocardial fibrosis is reduced with chronic inhibition of IL-18 in sickle mice (***P=0.0001).

The links between the presence of a systemic sickle cell phenotype and increased QTc and myocardial fibrosis have not been previously characterized. Circulating heme, increased oxidative stress, along with other injurious molecules (37-41) in sickle cell disease may increase predisposition to cardiac injury and cardiac fibrosis. Furthermore, hypoxia is a well-established inducer of hemolysis in sickle cell disease which may further exacerbate cardiac ischemia and injury and risk of developing ventricular arrhythmias; in experiments described herein, evidence to support this latter notion was observed after a 50% reduction in perfusion rate (FIG. 5A) which resulted in prolonged action potential duration with frequent PVCs (n=5/5 sickle mice) and PMVT spontaneously in one mouse. This finding underscores the need to screen sickle cell patients who suffer from acute hemolytic episodes for known risk stratifiers of ventricular arrhythmias such as prolonged QTc, myocardial ischemia (by ECG or cardiac enzymes for example), and evidence of myocardial fibrosis on imaging.

QTL analysis further validates the link between genetic and molecular mechanisms of IL-18 to QTc and outcomes in sickle cell disease. While rs360719 (in complete LD with previously reported (Hernesniemi et al., Eur Heart J. 2009; 30(23):2939-46; Hernesniemi et al., Atherosclerosis. 2008; 196(2):643-9) promoter SNP, r5187238) was not associated with QTc or IL18 expression eQTL analysis revealed a novel rare SNP, rs5744285, associated with both IL18 expression levels and QTc interval in sickle cell disease. The previously reported SNP, rs187238, was associated with sudden cardiac death in a non-sickle Caucasian heart failure cohort. The lack of this association may possibly stem from differences in linkage disequilibrium patterns between African and European populations. In addition, other SNPs as revealed by rs5744285 and rs11214107 may also influence IL18 expression which may be race-specific. Additionally, the sliding window haplotype analysis identified haplotypes that showed stronger association than a single SNP analysis alone, highlighting the significance of the top SNPs. The presence of a variant, rs5744285 that is cis-eQTL with IL18 expression further validates the role of IL18 in mediating prolonged QTc as well as associated poor outcomes.

Experiments described herein also link the chronic inhibition of IL-18 functionally to the improvement of myocardial fibrosis and diastolic dysfunction via modulating pro-inflammatory NFκB levels. Differential regulation between WT and sickle mice reveal several inflammatory pathways that are up-regulated in LV tissues of sickle mice including cytokine-cytokine receptor interactions, IgA production, primary immunodeficiency, and antigen processing and presentation. In fact, the acute influence of IL-18 may be further enhanced in the setting of a chronically injured and inflamed myocardium in sickle mice unlike WT mice.

Furthermore, the electrophysiology remodeling within sickle hearts resembles the concept of "reduced repolarization reserve" (Roden, Pacing Clin Electrophysiol. 1998; 21(5):1029-34) as has been previously proposed as a general condition that promotes long QT-related arrhythmias such as early after depolarizations and Torsades de Pointes with further stress. Specifically, expression data show significant reductions in KCND2 and KCND3 expression, encoding the alpha-subunits of the voltage-gated potassium channels Kv4.2 and Kv4.3 conducting the fast transient outward current (Ito,f). The functional knockout of Kv4.2 in mouse previously demonstrated prolonged QT, AV block and frequent VTs (44, 45) as seen in sickle mouse hearts with IL-18 infusion and pacing protocols. While other channels may also be involved in these repolarization abnormalities and channel activation and current may also influence this phenotype, PCR data do not show involvement of several other channels surveyed including other potassium and sodium channels.

Accordingly, provided herein are methods of characterizing, diagnosing, and treating arrhythmias (e.g., in patients with sickle cell disease).

Diagnostic and Characterizing Applications

In some embodiments, the present invention provides methods of diagnosing arrhythmias or other cardiac conditions (e.g., in subjects with sickle cell disease, sickle cell trait, hemolytic anemia, or increased levels of heme or IL-18 in circulation, blood samples, or tissue) based on the presence or absence of variant alleles of IL-18.

In some embodiments, methods provide a diagnosis of arrhythmia (e.g., ventricular arrhythmia). In some embodiments, methods provide a method of predicting an outcome in a subject selected from, for example, increased likelihood of developing ventricular arrhythmia, prolonged QTc time, myocardial fibrosis, or diastolic dysfunction. In some embodiments, methods characterize samples for the presence of variant IL-18 alleles (e.g., those described herein).

A. IL-18 Alleles

In other embodiments of the present invention, additional alleles of IL-18 are provided. In preferred embodiments, alleles result from a polymorphism or mutation (i.e., a change in the nucleic acid sequence) and produce altered mRNAs or polypeptides. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In some embodiments, variants are in the promoter region of IL-18. Exemplary variants and haplotypes include, but are not limited to, C at rs11214107; a haplotype of T at rs5744285 and C at rs11214107; a haplotype of C at rs11214107 and A at rs12796114; or a haplotype of G at rs5744285 and C at rs80008802.

B. Detection of IL-18 Alleles

In some embodiments, the present invention provides methods of detecting the presence of wild type or variant (e.g., mutant or polymorphic) IL-18 nucleic acids or polypeptides. The detection of mutant IL-18 finds use in the diagnosis of disease (e.g., arrhythmias).

Accordingly, the present invention provides methods for determining whether a patient has an increased susceptibility to cardiac disease by determining whether the individual has a variant IL-18 allele or increased level of wild type IL-18. In other embodiments, the present invention provides methods for determining an increased risk for cardiac disease (e.g., as compared to an individual without the variant or compared to the population in general) to an individual based on the presence or absence of one or more variant alleles of IL-18 (e.g., those described herein) and/or an increased level of IL-18 (e.g., wild type IL-18).

A number of methods are available for analysis of variant (e.g., mutant or polymorphic) or wild type nucleic acid sequences. Assays for detecting variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays and techniques are useful in the present invention. Additional detection assays are known to one of skill in the art.

A. Sample

Any patient sample containing IL-18 nucleic acids or polypeptides may be tested according to the methods of the present invention. By way of non-limiting examples, the sample may be tissue, blood, urine, semen, or a fraction thereof (e.g., plasma, serum, saliva, cardiac samples).

The patient sample may undergo preliminary processing designed to isolate or enrich the sample for the IL-18 nucleic acids or polypeptides or cells that contain IL-18. A variety of techniques known to those of ordinary skill in the art may be used for this purpose, including but not limited: centrifugation; immunocapture; cell lysis; and, nucleic acid target capture (See, e.g., EP Pat. No. 1 409 727, herein incorporated by reference in its entirety).

B. DNA and RNA Detection

The IL-18 variants of the present invention may be detected as genomic DNA or mRNA using a variety of nucleic acid techniques known to those of ordinary skill in the art, including but not limited to: nucleic acid sequencing; nucleic acid hybridization; and, nucleic acid amplification.

1. Sequencing

In some embodiments, nucleic acid sequencing methods are utilized (e.g., for detection of amplified nucleic acids). In some embodiments, in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety are utilized. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671956; U.S. patent application Ser. No. 11/781166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

3. Microarrays

In some embodiments, microarrays are utilized for detection of IL-18 nucleic acid sequences. Examples of microarrays include, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays. Arrays can also be used to detect copy number variations at al specific locus. These genomic micorarrys detect microscopic deletions or other variants that lead to disease causing alleles.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

4. Amplification

IL-18 nucleic acid may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315). Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

5. Detection Methods

Non-amplified or amplified IL-18 nucleic acids can be detected by any conventional means. For example, nucleic acid can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

B. Kits for Analyzing Risk of IL-18 Diseases

The present invention also provides kits for determining whether an individual contains a wild-type or variant (e.g., mutant or polymorphic) allele of IL-18. In some embodiments, the kits are useful for determining whether the subject is at risk of developing cardiac disease (e.g., arrhythmias). The diagnostic kits are produced in a variety of ways. In some embodiments, the kits contain at least one reagent useful, necessary, or sufficient for specifically detecting a mutant IL-18 allele or protein. In preferred embodiments, the kits contain reagents for detecting a truncation in the IL-18 polypeptide. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated or variant IL-18 proteins.

In some embodiments, the kit contains instructions for determining whether the subject is at risk for developing cardiac disease. In preferred embodiments, the instructions specify that risk for developing cardiac disease is determined by detecting the presence or absence of a mutant IL-18 allele in the subject, wherein subjects having an mutant allele are at greater risk for IL-18 disease.

The presence or absence of a disease-associated mutation in a IL-18 gene can be used to make therapeutic or other medical decisions. For example, couples with a family history of cardiac disease may choose to conceive a child via in vitro fertilization and pre-implantation genetic screening. In this case, fertilized embryos are screened for mutant (e.g., disease associated) alleles of the IL-18 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a IL-18 allele known to be associated with cardiac disease allows for early intervention.

In some embodiments, the kits include ancillary reagents such as buffering agents, nucleic acid stabilizing reagents, protein stabilizing reagents, and signal producing systems (e.g., florescence generating systems as Fret systems), and software (e.g., data analysis software). The test kit may be packages in any suitable manner, typically with the elements in a single container or various containers as necessary along with a sheet of instructions for carrying out the test. In some embodiments, the kits also preferably include a positive control sample.

D. Bioinformatics

For example, in some embodiments, a computer-based analysis program is used to translate the raw data generated by the detection assay (e.g., the presence, absence, or amount of a given IL-18 allele or polypeptide) into data of predictive value for a clinician. The clinician can access the predictive data using any suitable means. Thus, in some preferred embodiments, the present invention provides the further benefit that the clinician, who may not be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant IL-18), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing cardiac disease or a diagnosis of cardiac disease) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

II. Therapeutic Methods

In some embodiments, the present invention provides compositions and methods for treating and preventing cardiac disease (e.g., arrhythmias) in a subject (e.g., a subject with sickle cell disease) by inhibiting IL-18 expression or activity.

In some embodiments, prior to or during treating with an IL-18 inhibitor, subjects are screening for the presence of IL-18 variants (e.g., the ones described herein). In some embodiments, anti-IL-18 therapy is only administered to subjects with variant IL-18 genes. In some embodiments, IL-18 is administered to a subject in need thereof, regardless of IL-18 status. In some embodiments, anti-IL-18 therapy results in a decrease in IL-18 expression or activity.

The present disclosure is not limited to particular IL-18 inhibitors. Examples include, but are not limited to, a nucleic acid, a small molecule, peptide, or an antibody.

In some embodiments, the IL-18 inhibitor is a small molecule (e.g., hydroxyurea or decitabine). Hydroxyurea is commercially available (e.g., from Teva Pharmaceuticals, North Wales, Pa.). Decitabine is commercially available (e.g., from Otsuka America Pharmaceutical, Rockville, Md.).

In some embodiments, the IL-18 inhibitor is a nucleic acid. Exemplary nucleic acids suitable for inhibiting IL-18 (e.g., by preventing expression of IL-18) include, but are not limited to, antisense nucleic acids, miRNAs, and shRNAs.

In some embodiments, compositions comprising oligomeric antisense compounds, particularly oligonucleotides are used to modulate the function of nucleic acid molecules encoding IL-18, ultimately modulating the amount of IL-18 expressed. This is accomplished by providing antisense compounds that specifically hybridize with one or more nucleic acids encoding IL-18. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of IL-18. In the context of the present disclosure, "modulation" means either an increase (stimulation) or a decrease (inhibition) in the expression of a gene. For example, expression may be inhibited to treat or prevent a metabolic disorder.

In some embodiments, nucleic acids are siRNAs. "RNA interference (RNAi)" is the process of sequence-specific, post-transcriptional gene silencing initiated by a small interfering RNA (siRNA). During RNAi, siRNA induces degradation of target mRNA with consequent sequence-specific inhibition of gene expression.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, SIN3A. As used herein, the term "siRNA" is a generic term that encompasses all possible RNAi triggers. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding SIN3A. In some embodiments, the length of the duplex of siRNAs is less than 30 base pairs. In some embodiments, the duplex can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the duplex is 19 to 32 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

As used herein, Dicer-substrate RNAs (DsiRNAs) are chemically synthesized asymmetric 25-mer/27-mer duplex RNAs that have increased potency in RNA interference compared to traditional siRNAs. Traditional 21-mer siRNAs are designed to mimic Dicer products and therefore bypass interaction with the enzyme Dicer. Dicer has been recently shown to be a component of RISC and involved with entry of the siRNA duplex into RISC. Dicer-substrate siRNAs are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miR-NAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (.about.35 nucleotides upstream and .about.40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The present disclosure contemplates the use of any genetic manipulation for use in modulating the expression of IL-18. Examples of genetic manipulation include, but are not limited to, gene knockout (e.g., removing the IL-18 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably 108 to 1011 vector particles added to the perfusate.

In some embodiments, the present disclosure provides antibodies that inhibit IL-18. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, candidate IL-18 inhibitors are screened for activity (e.g., using the methods described in Examples 1 and 2 below or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present disclosure the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXPERIMENTAL

The following examples are provided in order to demonstrate and further illustrate certain preferred embodiments and aspects of the present invention and are not to be construed as limiting the scope thereof.

Example 1

A. Methods

Sickle Cell Disease Patient cohort: Adult African American sickle cell disease patients were recruited prospectively from outpatient clinics at the University of Chicago (UCH) and at the University of Illinois at Chicago (UIC). All subjects provided informed written consent to participate in this study with the approval by the respective institutional review boards as previously published (Zhang et al., *Circulation.* 2014; 129(16):1650-8). Hemoglobin genotype was demonstrated by high-performance liquid chromatographic separation or gel electrophoresis for all patients. For phlebotomy, subjects were excluded if they were clinically unstable, defined by having vaso-occlusive crisis, acute chest syndrome, or unscheduled blood transfusions within 3 weeks of the study. All subjects over the age of 18 were considered for inclusion.

UCH cohort: All patients (n=23) underwent a prospective cardiac magnetic resonance (CMR) imaging with late gadolinium enhancement (LGE) sequence and phlebotomy draw as a same day procedure (Desai et al., *Circ Cardiovasc Imaging.* 2014; 7(3):430-7). The details of the imaging and microarray processing have been previously published (Desai et al., 2014; surpa).

UIC cohort: For each subject (n=153), the latest available ECG in normal sinus rhythm were included up until Dec. 31, 2014. ECG measurements were collected retrospectively from both inpatient and outpatient settings associated with adult sickle cell disease programs as previously described (Indik et al., *Br J Haematol.* 2016). Subjects were followed for vital status assessment up to Dec. 31, 2014 using social security index, phone calls and review of electronic medical records.

Electrocardiography: ECGs were performed as previously described (Indik et al., *Br J Haematol.* 2016) with a standard 12-lead configuration at 25 mm/s paper speed and 10 mm/MV amplitude, using a commercially available system (GE Muse).

Animal Work: Homozygous sickle cell disease model mice (JAX stock #013071 B6; 129—Hbatm1 (HBA)Tow Hbbtm2(HBG1,HBB*)Tow/tm2(HBG1,HBB*)Tow/J) and non-sickling control (B6; 129—Hbatm1(HBA)Tow/tm1 (HBA)Tow, Hbbtm3(HBG1,HBB)Tow/tm3(HBG1,HBB)/J were obtained from The Jackson Laboratory and all experiments were performed between the 10-14 weeks of age in male mice. Animals were handled in accordance with the NIH Guide for the Care and Use of Laboratory Animals. All protocols involving animals were approved by the Animal Studies Committee at the University of Illinois at Chicago, University of Wisconsin, Lifespan Animal Welfare Committee in Rhode Island Hospital, and the University of Arizona.

Surface Electrocardiogram Recording and Programmed Ventricular Stimulation in vivo: Surface electrocardiograms (ECGs) were recorded and ventricular arrhythmia inducibility was determined in WT and sickle mice using described methods (Rutledge et al., *J Am Coll Cardiol.* 2014; 63(9): 928-34) under general anesthesia with isofurane.

Optical mapping: WT and sickle male mice (12-16 weeks) hearts underwent optical mapping. The optical apparatus has been previously described (Rutledge et al., 2014; supra). The values are presented as the mean±standard deviation. Student t test was used and a P value of <0.05 was considered statistically significant. Sample activation potential traces and activation maps with BCL pacing were made for both the control and sickle cell hearts.

Ventricular conduction velocity measurement: LV conduction velocity was measured in anesthetized WT (n=5) and sickle mice (n=5) using a flexible multielectrode array (Flex-MEA, 72 electrodes) system (Multichannel systems, Reutlingen, Germany) according to manufacturer's instructions. Mid-anterior LV epicardial electrical propagation with a concentric bipolar electrode was recorded under right-ventricular pacing (750 bpm); the color mapping of LV conduction propagation, as well as the calculation of elliptical propagation and longitudinal (CVL) and transverse conduction velocities (CVT) were measured using Cardio 2D software (Multichannel systems, Reutlingen, Germany) (Rutledge et al., 2014; supra).

RNA preparation and microrarray processing. Human: Blood was drawn via peripheral venipuncture and care was taken to standardize blood sample collection and preparation. Peripheral blood mononuclear cells (PBMCs) were isolated from blood and stored at −80° C. as described previously (Desai et al., *Am J Respir Crit Care Med.* 2012). Total RNA was isolated from these lysates using Qiagen's RNeasy plus kit as per the manufacturer's directions. Both the Affymetrix Human Exon 1.0 ST arrays (UCH cohort) and Affymetrix Human Gene 2.0 ST arrays (UIC cohort) were utilized for expression profiling. Mouse: LV tissue was dissected from sickle (n=3) and control (n=3) mice, total RNA was isolated and hybridized to Affymetrix GeneChip Mouse Gene 2.0 ST arrays. Samples were RMA normalized in R (package: "oligo") and the coefficient of variation was used to remove the least variable 30% of probes. Differentially expressed genes between the two groups were identified using a two-sided, unpaired t-test (p<0.05). KEGG pathway enrichment was calculated by GSEA (50) with FDR<0.05.

Genotyping. From the UIC cohort, genotyping was performed using Affymetrix PanAFR array. Individuals with >95% missing genotypes and related individuals identified through identity-by-decent analysis were removed. Single nucleotide polymorphisms (SNPs) with genotyping call rate<95%, Hardy-Weinberg Equilibrium P<0.001, minor allele frequency<1% were also excluded. To identify SNPs that are cis-eQTL with IL18 and associated with QTc, 97 SNPs were analyzed within the IL18 gene as well as 100 kb up- and down-stream of the IL18 gene.

Genetic and Genomic Analyses. Within the UIC cohort, association between SNPs, IL18 gene expression, and phenotypes (QTc and mortality) were performed. Association between the levels of IL18 gene expression and QTc intervals were determined from all patients in the UIC cohort with available PBMC-derived microarray genome-wide gene expression profiles and a QTc value measured within 1 year of PBMC collection (n=32). Data were analyzed by maximal information-based nonparametric exploration (MINE) statistics described previously (51) to capture non-linear relationships. Maximal Information Coefficient (MIC) was extracted from the software output and statistical significance was estimated from pre-calculated p-value tables of MIC scores [http://www.exploredata.net/Downloads/P-Value-Tables, (51)] corresponding to sample size and interpolated by smooth spline (smooth.spline and predict in R). MIC scores range from 0 (no association between variables) to 1 (100% dependency between variables). To determine linear relationships between QTc and IL18 expression, since QTc deviated from normal distribution, a Mann-Whitney U test was also performed.

Linear relationship between IL18 SNP minor allele dosage and IL18 gene expression (cis-eQTL) was tested using the log 2-normalized expression as well as log-transformed QTc values as a dependent variable in a linear regression model adjusting for age, gender, hemoglobin genotypes (SS vs. others), and the first principal component. Principal component analysis was performed using Golden Helix SVS 8.4.1. While P<5.15×10$^{-4}$ indicates region-wide significance, in single SNP analysis, P<0.05 was considered as nominally significant. Haplotype association tests were performed using two different approaches. First, haplotypes containing two SNPs that were strongly associated SNPs from each analysis (IL18 expression and QTc) using E-M algorithm were estimated. Second, a sliding window-based approach was employed for haplotype containing two, three, and four SNPs. Haplotype association was tested with logistic regression analysis, and empirical P values were obtained through 10,000 permutations. Within the UIC cohort, relationship between IL18 expression levels and mortality (n=138) was examined. Binary logistic regression analysis was performed using tertiles of IL18 expression levels adjusting for age (age of death or age at mortality assessment), gender, hydroxyurea use, hemoglobin genotype, and BMI. Statistical analyses were performed using PLINK (52) and SPSS Version 23 (IBM Corp, Armonk, N.Y.). Within the UCH cohort, Significance Analysis of Microarrays (SAM) (53) (54), implemented in the samr library of the R Statistical Package (55), was used to conduct group-wise comparison on log 2-transformed gene expression levels between those patients who demonstrated LGE on CMR and those who did not. False discovery rate (FDR)

was controlled using the q-value method (56). Transcripts with a fold-change >1.2 and FDR <10% were deemed differentially expressed.

Western blotting, RT-PCR, Immunofluorescence and Immunohistochemistry: Total protein lysates, RNA, and tissue for histology were extracted from the left ventricle of 10-12 week-old WT control and sickle male mice.

Statistics: All measurements were presented in means±SEM with P values<0.05 considered statistical significance. The inducibility of VT was presented as percentage of all tested animals in the same group. The statistical significance of differences between experimental groups was evaluated by the exact version of the Mann-Whitney U test or Fisher's exact test, followed by Holm test to correct for multiple comparisons unless otherwise specified.

Results

Immunohistochemistry and immunofluorescence microscopy of mouse hearts reveal increased patchy myocardial collage deposition and fibrosis in sickle mice compared to control mice (FIGS. 1A and 1B). Electrical mapping of WT (FIG. 1D) and sickle mice (FIG. 1E) ex vivo revealed longer action potential duration (APD, FIG. 1C-representative, FIG. 1F), reduced longitudinal (FIG. 1G) and transverse (FIG. 1H) conduction velocity (CV) in sickle mice hearts with no significant changes in rise-time of action potentials (FIG. 1I). ECG data in vivo confirmed sickle mice have longer monophasic APDs, effective refractory periods, and T wave repolarization intervals with similar heart rates compared to WT mice.

Figure 2:
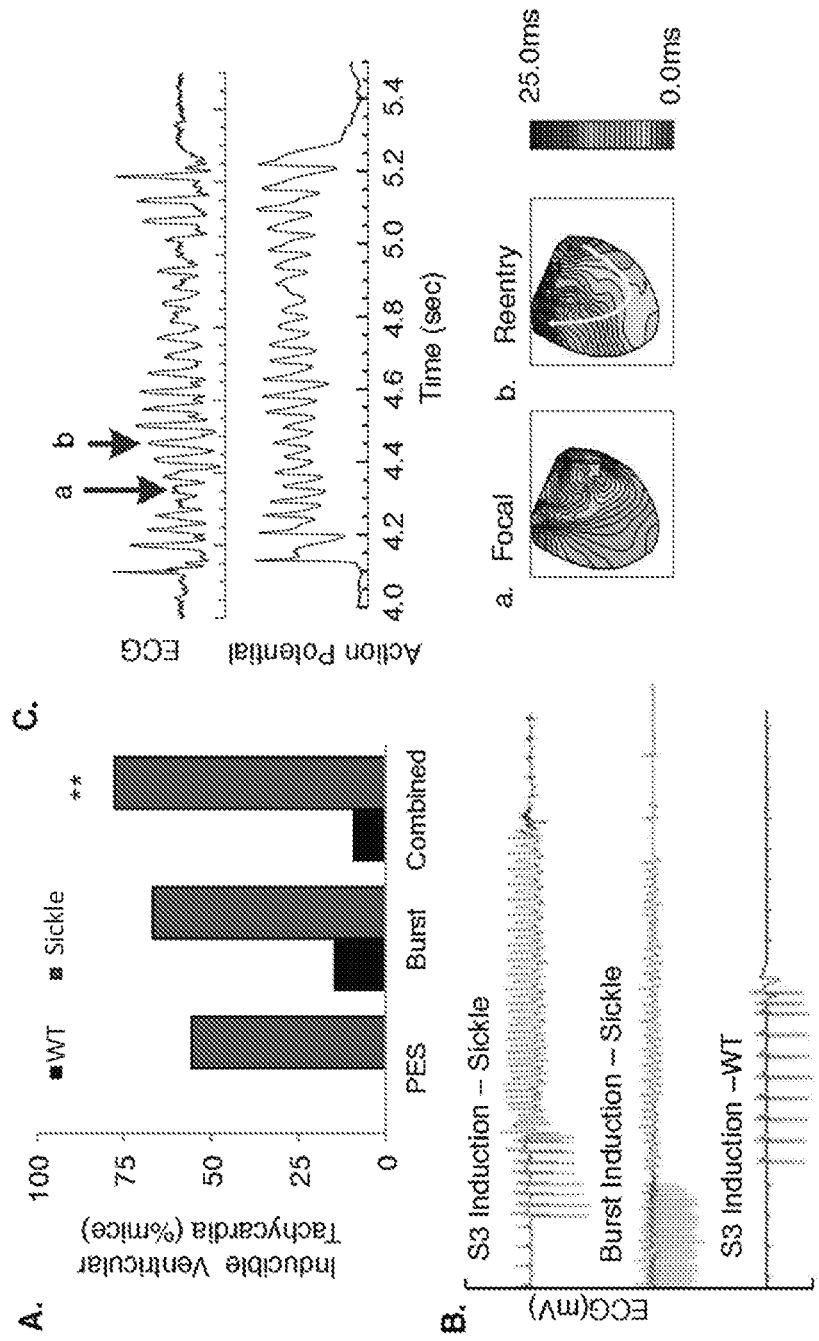
FIG. 2A-C shows that sickle mice are susceptible to ventricular arrhythmias. A. Using in vivo catheter-inducibility testing with programmed and burst pacing protocols, sickle mice demonstrated significantly more episodes of polymorphic VT compared to WT mice (sickle-7/9 mice, WT, 1/11 mice, **P=0.0018). B. Tracings of polymorphic VT in sickle mice and PVC in WT mice after programmed and burst induction. C. An example of VT observed from one sickle cell mouse exposed to 50% perfusion flow during optical mapping. Detailed activation maps indicated that VTs were maintained by focal activity (a) and reentry (b).

Based on the presence of myocardial fibrosis and prolonged APD, inducibility testing for arrhythmias in vivo was performed using programmed and burst pacing protocol (FIG. 2A) and revealed a significantly greater propensity for polymorphic ventricular tachycardia (VT, P=0.0045) in sickle mice (77.8% mice) compared to WT mice (11.1%) with pacing (P=0.0018). Sickle mice exhibited frequent VTs that last longer during both stimulation protocols. Examples of VT visualized after burst and PES pacing are illustrated in FIG. 2B. These data confirm that sickle mice are predisposed to polymorphic VT.

Hypoxia can aggravate myocardial ischemia and induces hemolysis in sickle cell patients. Hemolysis has been reported to be associated with prolonged QTc (Indik et al., *Br J Haematol.* 2016). Reducing the perfusion rate during optical mapping from 3 mL/min to 1.5 mL/min (50% reduction) to mimic a lower oxygen supply state caused frequent PVCs in sickle cell hearts (n=5/5 hearts, compared to control (n=0/4 hearts). The activation maps of PVCs showed a focal source in the ventricle that propagated to the rest of region. In one sickle heart (n=1/5), the presence of PVCs and induced VT was detected. The activation maps (FIG. 2C) revealed that VTs were maintained by focal activity that that propagate and form functional and varying reentrant circuits. These data indicate that myocardial ischemia may predispose to ventricular arrhythmias in sickle cell disease.

Figure 3:
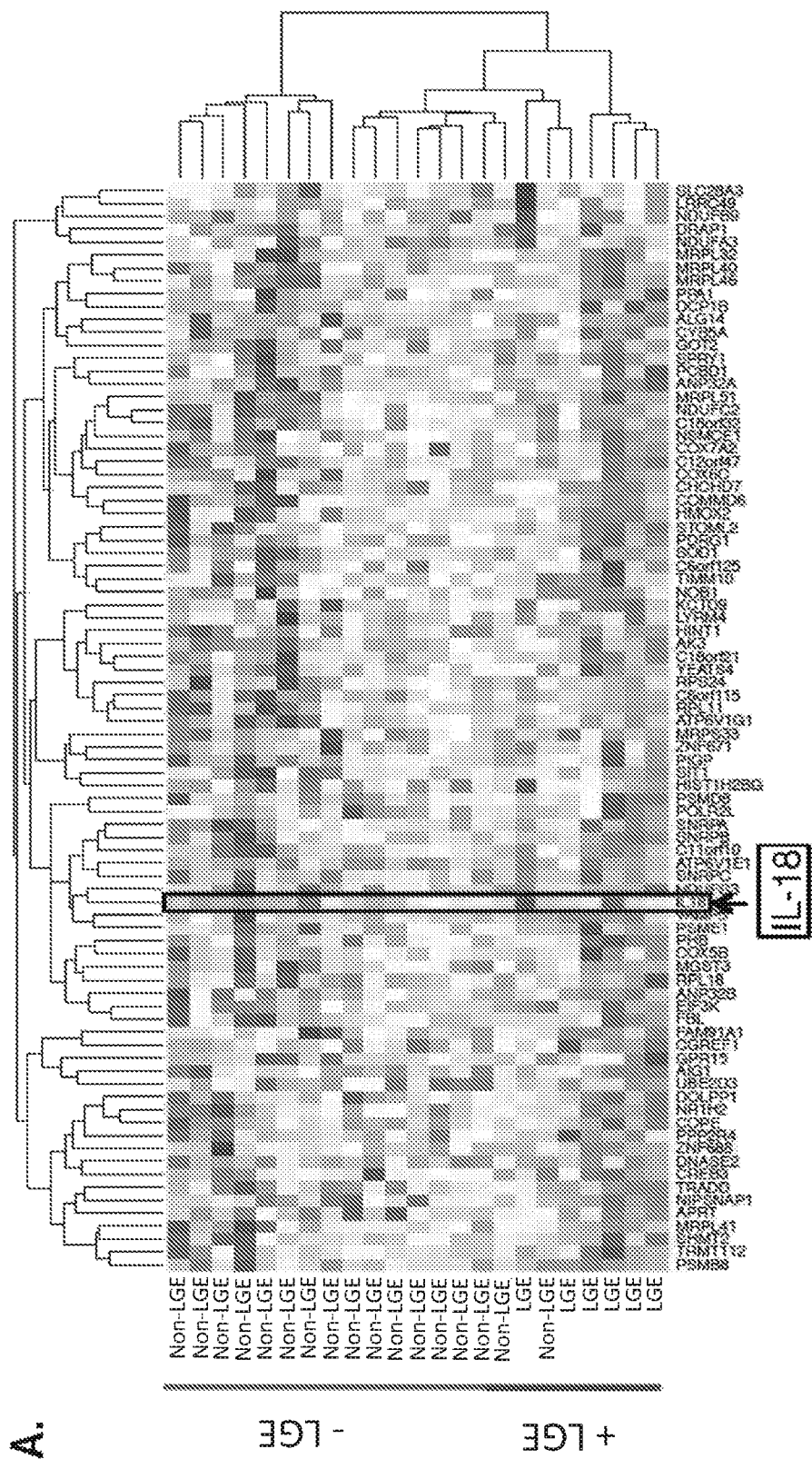
FIG. 3A-B shows that IL-18 is associated with myocardial fibrosis in sickle cell disease.
A. Microarrays performed on PBMC-derived RNA in patients with sickle cell disease revealed a unique set of genes, which were differentially regulated between those patients that exhibited evidence of myocardial fibrosis on cardiac MM and those patients that did not have any evidence. B. Histologic examination of myocardium collected from sickle cell patient autopsies revealed increasing IL-18 staining in those patients with a greater degree of fibrotic burden.

To determine the molecular underpinnings of this fibrotic cardiomyopathy, sickle cell disease patients were assessed for differential gene expression in circulating PBMCs. In the UCH cohort, patients prospectively underwent cardiac MRI with LGE imaging to detect myocardial fibrosis. Evaluation of peripheral blood mononuclear cells (PBMC)-derived gene expression profiling in sickle cell disease patients with and without evidence of myocardial fibrosis (presence of LGE) on cardiac MRI revealed 84 differentially expressed genes (FIG. 3A) including high levels of IL18 expression. This latter observation validates previous reports on IL-18 as an established pro-fibrotic inflammatory mediator (Xing et al., Mol Med. 2010; 16(11-12):465-70). Histologic examination of three available human myocardial autopsy specimens from patients with sickle cell disease further supported these observations by demonstrating increased IL-18 staining in patients with a greater myocardial fibrosis burden (FIG. 3B). Taken together, these data demonstrate that circulating and cardiac IL-18 is a candidate gene for cardiac fibrosis in sickle cell disease.

Figure 4:
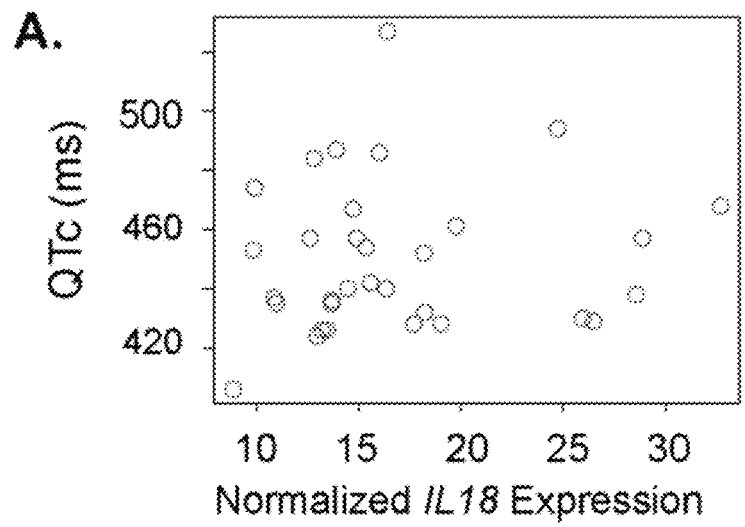
FIG. 4A-E shows that IL-18 is associated with prolonged QTc and mortality in sickle cell disease. A. QTc is associated with IL18 transcript expression. B. Circulating PBMC-derived IL18 expression was significantly elevated at steady-state in patients who later died compared to those who survived (*P=0.04). C. A candidate gene analysis of regional SNPs near the IL18 gene reveal top SNPs associated with IL18 gene expression including rs5744285 (P=0.003). D. IL18 gene reveal top SNPs associated with prolonged QTc including rand rs5744285 (P=0.012). E. The CT genotype of rs5744285 was associated with decreased IL-18 gene expression compared to the CC genotype (P<0.05).
Figure 4:
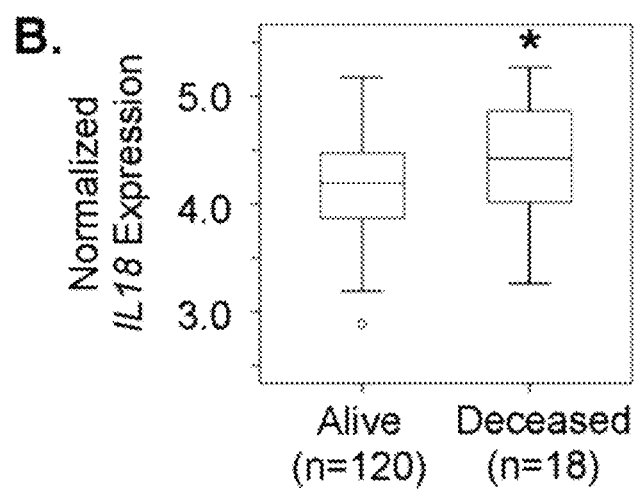
Figure 4:
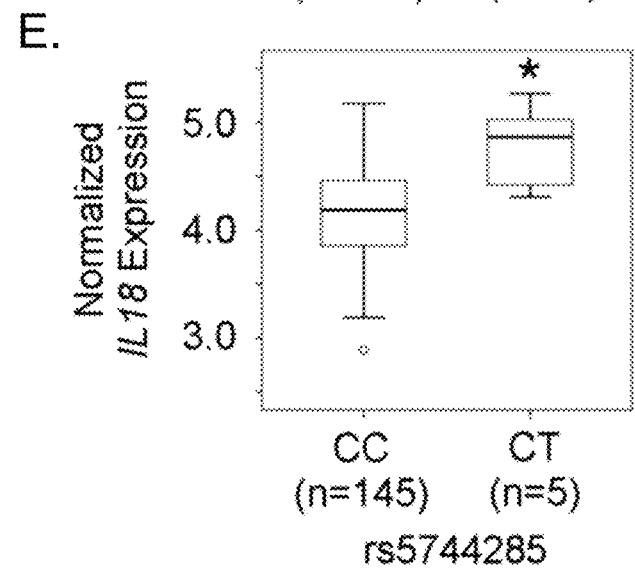
Figure 4:
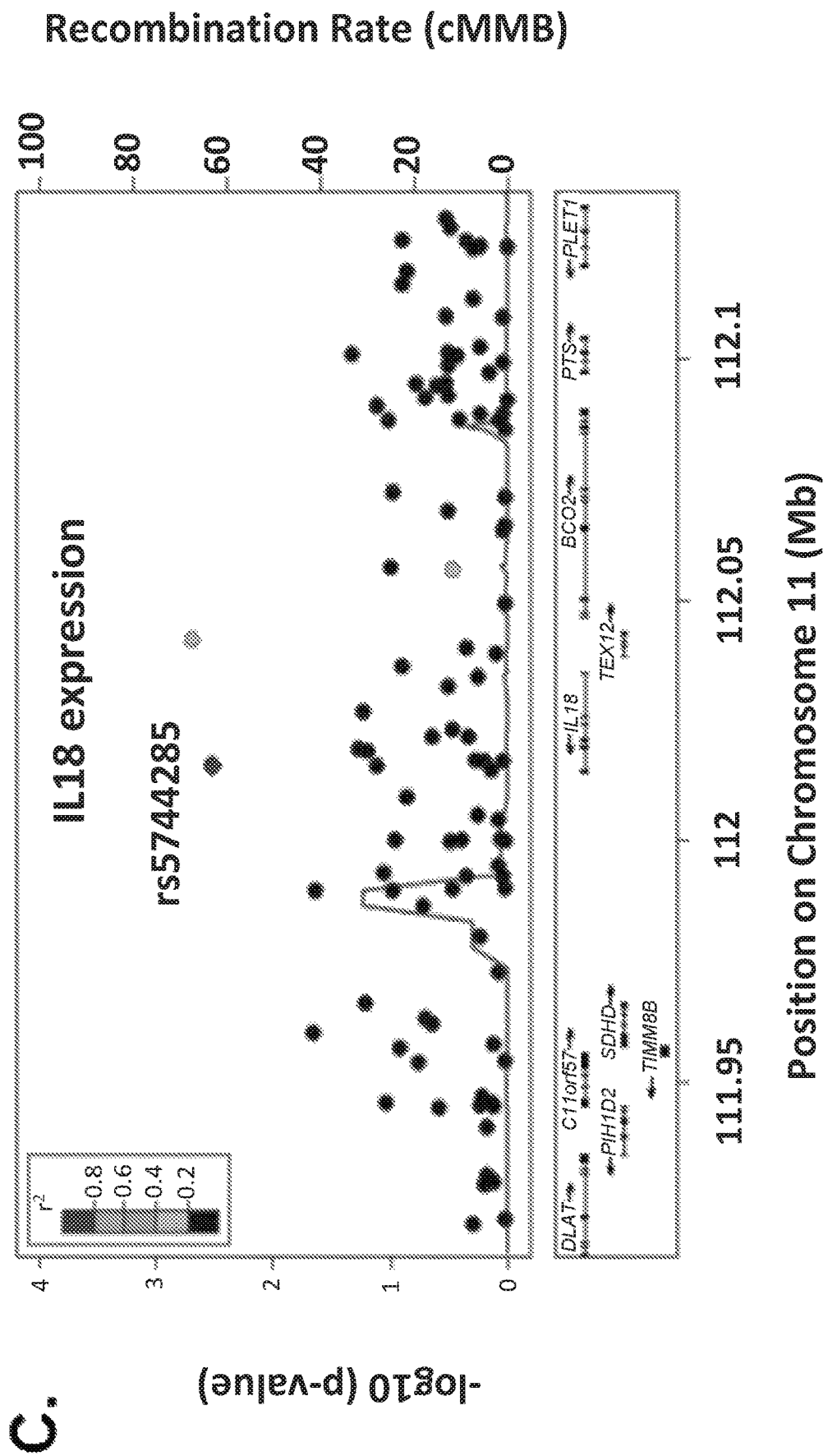
Figure 4:
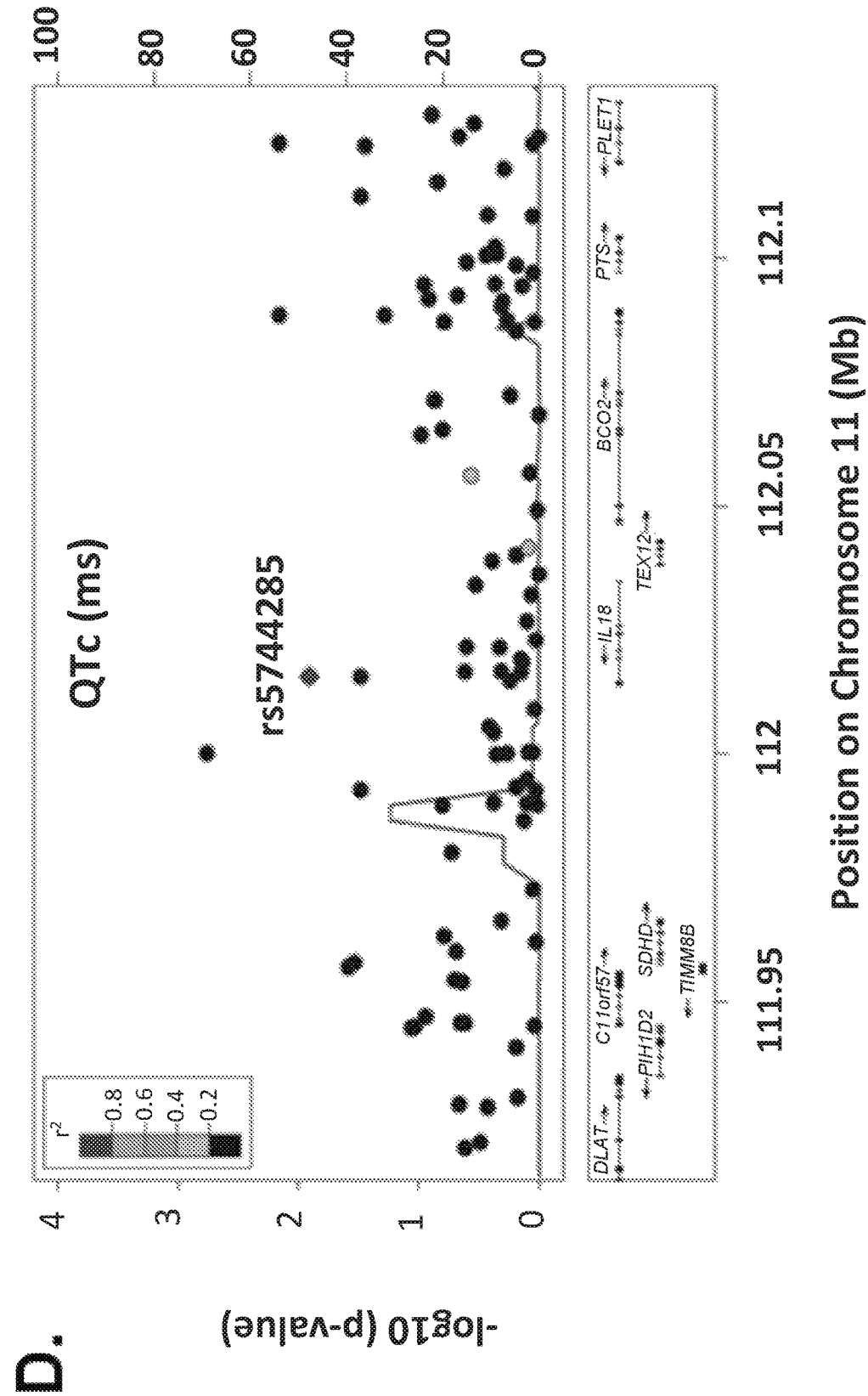

While IL-18 has an established relationship with fibrosis, it was investigated whether this cytokine could also be contributing to the prolonged QTc interval. Using available microarray data from the UIC cohort, linear and nonlinear analyses were performed to determine relationships between IL18 transcript levels and QTc. Among all patients with hemoglobin SS genotype who underwent an ECG prospectively within one year after blood collection, Maximal Information Coefficient statistics found a significant non-linear association (MIC=0.42; p=0.04; FIG. 4A). These data were further corroborated by using a Mann-Whitney U test revealing significantly higher QTc levels in patients classified as having higher IL18 expression (median QTc 430.5+29.0 vs. 452.0 ms+32.0, P=0.047).

Consistent with IL-18 being associated with long QTc, IL-18 levels also portend risk of mortality in sickle cell disease. In the UIC cohort, PBMC-derived IL18 gene expression was evaluated among patients who were prospectively followed for outcomes and vital status. In univariate analysis, sickle cell patients who died had higher PBMC-derived IL18 expression levels than those who survived (FIG. 4B; mean IL18 expression 4.39+0.55 vs. 4.15+0.43, P=0.04). In multivariable regression analysis adjusting for age, gender, hydroxyurea use, hemoglobin genotype, and body mass index, IL18 expression was positively associated with mortality where patients in the highest tertile of IL18 expression had significantly increased odds of mortality compared to patients in the lowest tertile of IL18 expression (OR=5.36, 95% CI 1.07-26.76, P=0.04). These data cumulatively indicate that PBMC-derived circulating IL18 expression levels may be a novel predictive biomarker of mortality risk in sickle cell disease.

Based on previously published reports of IL18 promoter SNP (r5187238) associated with sudden cardiac death in a non-sickle cell patient population (Hernesniemi et al., *Eur Heart* 2009; 30(23):2939-46; Hernesniemi et al., *Atherosclerosis*. 2008; 196(2):643-9), genetic variation was assessed to determine whether IL18 SNPs are associated with IL18 expression and prolonged QTc in sickle cell patients. Genotype and expression data were available for 153 patients in the UIC cohort; genotype and ECG data (collected retrospectively and prospectively) were available for 124 patients. While no SNPs demonstrated region-wide significance with IL18 expression or with QTc interval (Tables 1 and 2), a novel SNP, rs5744285, was identified and associated with both IL18 expression (nominal P=0.003, FIG. 4C) and QTc (nominal P=0.012, FIG. 4D).

rs5744285 showed the second strongest signal of association with IL18 expression. Mean IL18 expression among patients with a CT genotype was 4.78, while patients with a CC genotype demonstrated a mean expression level of 4.17 (FIG. 4E). An additional SNP in the promoter region, rs11214107 (r2=0.0 with rs187238 which was not on the platform) was the most strongly associated with IL18 expression levels (P=0.002, FIG. 4C), but this SNP was not associated with QTc (P>0.05).

To evaluate for additive effects, associations of haplotypes containing two SNPs were evaluated. Linkage disequilibrium was calculated for the regional SNPs (r2=0.14 between rs5744285 and rs11214107, r2=0.06 between rs5744285 and rs112708928). Based on associations of IL18 expression levels with the alllelic distributions in the SNP analysis, the CT (major alleles) halpotype of rs5744285 (T) and rs11214107 (C) showed a strong association and was associated with decreased IL18 expression ($\beta$=−0.29; P=0.002) and decreased QTc ($\beta$=−0.019; P=0.0004) levels compared to all other haplotypes. Since $\beta$ coefficient and P values obtained from haplotype analysis were similar to those from single SNP analysis, a sliding window analysis was next performed to increase power. The haplotype CA for rs11214107 and rs12796114 exhibited the strongest association with increased IL18 expression levels ($\beta$=0.35, P=0.001) while haplotype GC from rs5744285 and rs80008802 was associated with decreased QTc levels ($\beta$=−0.03; P=0.0008). These two haplotypes remained significant after adjusting for multiple testing and 10,000 permutations. These data indicate that IL18 is associated with prolonged repolarization in sickle cell disease and patients with the CT genotype at rs5744285 have increased levels of IL18 gene expression with greater likelihood of developing prolonged QTc.

To establish cause and effect, acute effects of IL-18 on the myocardial electrical phenotype were evaluated further in sickle mice. Exogenous administration of IL-18 via the perfusate (20 ng/min) resulted in prolonged APD (FIG. 5A), reduced trends in CV (FIGS. 5B and 5C), and increased rise time (FIG. 5D) in sickle mice with no significant changes observed in WT mice. Typically after 20 minutes, IL-18 administration led to APD prolongation, atrioventricular block, and a slowed heart rate. Longer perfusion of IL-18 led to the development of multiple PVCs and short-lived VTs (n=4/4 hearts, FIG. 5E). Analysis of action potentials revealed that PVCs were initiated before the previous action potential fully repolarized, indicating that prolonged APD under IL-18, resulted in early after-depolarizations. These intact heart mapping data indicate that prolongation of APD and slowing CV in sickle cell hearts stem from electrophysiological remodeling that creates a vulnerable environment for the development to arrhythmias.

Figure 6:
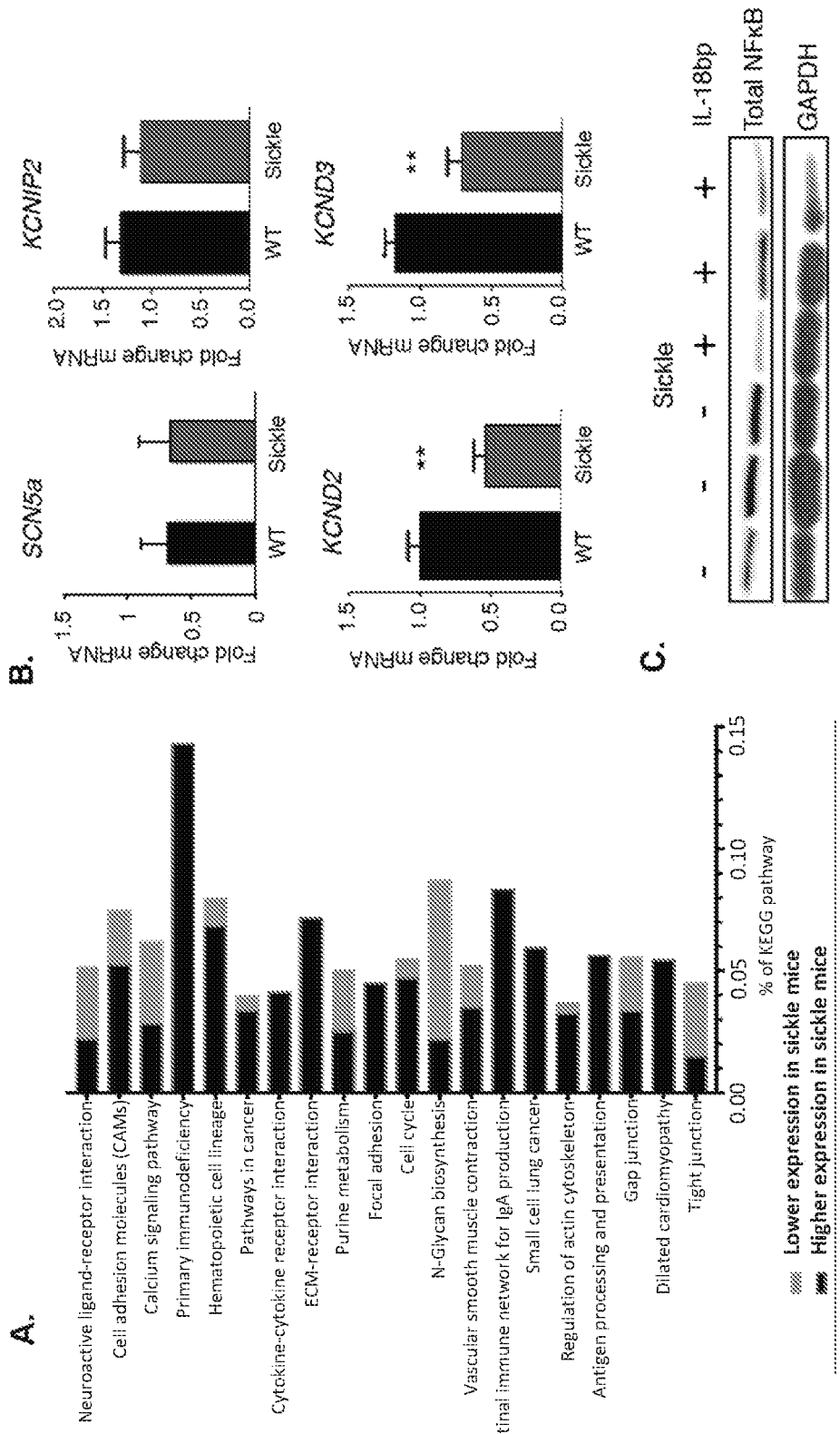
FIG. 6A-C shows differential myocardial channel expression in sickle cell and WT mice. A. Genome-wide microarray-based gene expression profiling was performed in LV tissue and revealed the top differentially-regulated pathways between WT and sickle mice B. An RT-PCR survey of various cardiac channels revealed decreased KCND2 (P=0.01) and KCND3 (P=0.01) in sickle vs WT mice. C. Western blot data revealed reduced myocardial NFkB expression in sickle mice exposed to chronic IL-18 inhibition compared to vehicle.

Based on the association of IL-18 with myocardial fibrosis and diastolic dysfunction, the functional role of IL-18 in the development of myocardial fibrosis and diastolic dysfunction was tested. Chronic inhibition of IL-18 with IL-18 bp, which binds to IL-18 and prevents it from activating its receptor, resulted in reduced myocardial fibrosis (FIG. 5Q) and improved echocardiogram-indices of diastolic function (FIG. 5) in sickle mice. These data validate what has been previously noted (Xing et al., *Mol Med.* 2010; 16(11-12): 465-70; Hernesniemi et al., *Eur Heart J.* 2009; 30(23):2939-46; Hernesniemi et al., *Atherosclerosis.* 2008; 196(2):643-9; Wang et al., *Shock.* 2008; 30(1):3-10; Platis et al. *Perfusion.* 2008; 23(4):237-42; Pomerantz et al., *Proc Natl Acad Sci USA.* 2001; 98(5):2871-6; Gu et al., *Transpl Int.* 2015; 28(12):1436-44; Blankenberg et al., *Circulation.* 2003; 108 (20):2453-9; Blankenberg et al., *Circulation.* 2002; 106(1): 24-30; Hartford et al., *Arteriosclerosis, thrombosis, and vascular biology.* 2010; 30(10):2039-46) regarding the role of IL-18 in the improvement of myocardial diastolic function. The mechanisms of how IL-18 mediates sickle cardiomyopathy with prolonged repolarization, diastolic dysfunction, and myocardial fibrosis are unclear. Given the absence of significant IL-18 effect on WT mice and the vulnerability of sickle mice, microarray transcript profiling in murine LV tissue between the two mice was performed. A total of 1611 probes (812 annotated genes) were differentially expressed between sickle and WT mice (P≤0.05). Gene set enrichment analysis identified 26 significantly enriched KEGG pathways (FIG. 6A). Sickle mice had higher expression of inflammatory genes and showed dysregulation of calcium signaling, cytokine and cytokine receptor interactions, and gap junctions as the top differentially regulated pathways. Additionally, RT-PCR and western blot reveal sickle mice have reduced myocardial KCND2 and KCND3 gene expression levels (FIG. 6B) consistent with increased APD. Furthermore, with chronic IL-18 inhibition, NFκB levels (FIG. 6C) are significantly reduced. Expression of other surveyed sodium and potassium channels previously associated with VT (Yang KC, Kyle J W, Makielski J C, and Dudley S C, Jr. Mechanisms of sudden cardiac death: oxidants and metabolism. *Circ Res.* 2015; 116(12):1937-55) were not significantly altered. These data reveal that multiple baseline mediators are associated with sickle mouse cardiomyopathy and NFκB induction is, in part, associated with IL-18 mediated susceptibility to sickle cell cardiomyopathy.

TABLE 1

Regional IL18 SNPs associated with IL18 expression

| SNP | Physical Positions(BP) | Minor Allele | β | P |
|---|---|---|---|---|
| rs11214107 | 112041597 | C | 0.290 | 0.002 |
| rs5744285 | 112015647 | T | 0.620 | 0.003 |
| rs73568086 | 111960138 | G | 0.214 | 0.02 |
| rs360726 | 111989592 | C | −0.120 | 0.02 |
| rs12291603 | 112100834 | C | −0.203 | 0.05 |
| rs5744264 | 112019165 | T | 0.250 | 0.05 |
| rs360722 | 112026703 | A | 0.117 | 0.06 |
| rs693441 | 111966307 | T | −0.112 | 0.06 |
| rs5744266 | 112018525 | A | 0.243 | 0.06 |
| rs57244711 | 112090205 | T | 0.139 | 0.08 |
| rs80008802 | 112015578 | T | −0.419 | 0.08 |
| rs4592454 | 111993268 | A | −0.087 | 0.09 |
| rs59038861 | 111945610 | A | 0.100 | 0.09 |

TABLE 2

Regional IL18 SNPs associated with QTc

| SNP | Physical | Minor Allele | β | P |
|---|---|---|---|---|
| rs112708928 | 112000099 | C | 0.018 | 0.002 |
| rs113614882 | 112088513 | C | 0.036 | 0.007 |
| rs78301418 | 112123280 | C | 0.036 | 0.007 |
| rs5744285 | 112015647 | T | 0.026 | 0.012 |
| rs14396 | 111956989 | C | 0.014 | 0.03 |
| rs7121782 | 111957819 | T | −0.008 | 0.03 |
| rs113583301 | 112112478 | C | −0.029 | 0.03 |
| rs360724 | 111992673 | A | −0.017 | 0.03 |
| rs80008802 | 112015578 | T | 0.029 | 0.03 |
| rs116108036 | 112122752 | G | −0.028 | 0.04 |
| rs2217401 | 112088499 | A | −0.014 | 0.05 |
| rs79835487 | 111944702 | C | −0.010 | 0.09 |
| rs2303437 | 111944901 | T | −0.007 | 0.09 |

Example 2

Functional Validation of Heme-Mediated IL18 Promoter SNPs on Promoter Activity

Studies have revealed that increased hemolysis is associated with prolonged QTc and circulating IL-18 levels in sickle cell patients (Cerqueira et al., *Cytokine* 56:471-476.), both factors associated with increased risk of mortality. Prior published data have also shown a promoter SNP (r5187238) that is associated with increased IL18 expression levels and sudden cardiac death in Caucasians (Hernesniemi et al., 2008. *Atherosclerosis* 196:643-649; Hernesniemi et al., 2009. *Eur Heart J* 30:2939-2946). Analysis of the sickle cell GWAS (Gupta et al., 2016. *JCI Insight*) revealed rs187238 was not on the platform; however, based on regional (+/−10 kb) analysis of SNPs near the IL-18 gene, a novel SNP in the promoter region and two IL18 promoter-containing haplotypes associated with prolonged QTc and PBMC-derived IL18 expression in patients with sickle cell disease were identified (See Example 1). Based on 1000 Genomes, several promoter SNPs over-represented in populations of African Descent (ADs) compared to European Descent (EDs) were identified.

IL18 promoter regions, transcription factor (TF) binding, and SNPs influenced by cell exposure to heme are identified using THP-1 cells, a well-established monocyte cell line, exposed to heme and transfect with promoter luciferase reporter constructs (Sun et al., 2014. *Am J Respir Cell Mol Biol* 51:660-667; Ye et al., 2005. *Am J Respir Crit Care Med* 171:361-370). Promoter binding sites of B-cell lymphoma 6 protein (BCL6), a master zinc finger TF established as transcriptional repressor for the IL18 gene are also evaluated (Zhang et al., 2008. *FEBS Lett* 582:1802-1808).

Figure 7:
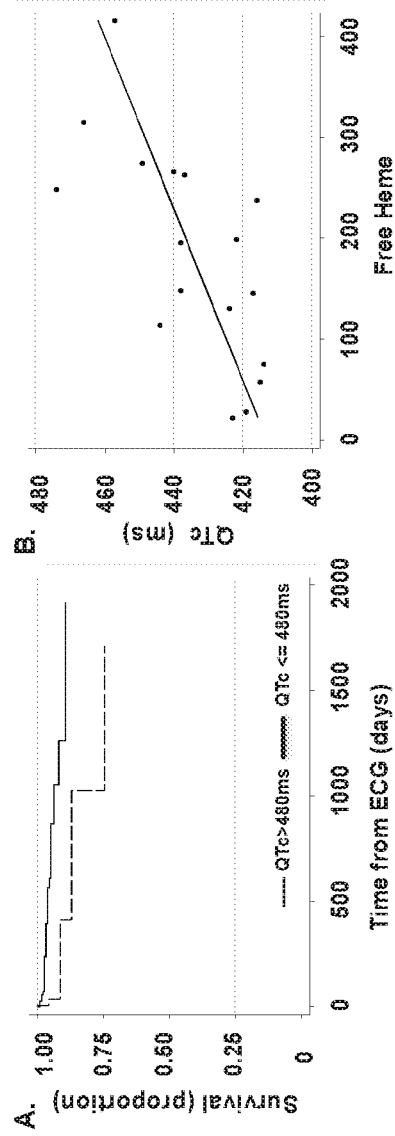
FIG. 7A-B shows that prolonged QTc is correlated with free heme and sickle cell mortality. A. Kaplan-Meier survival curves display worse survival for sickle cell disease patients with prolonged QTc (n=224), P=0.034. B. QTc is positively associated with plasma measured free heme levels in patients with sickle cell disease (n=16). P=0.002

Table 3 details IL18 promoter SNPs that were either over-represented in populations of AD compared to ED, known to increase IL18 gene expression, or associated with either prolonged QTc or sudden cardiac death (Hernesniemi et al., 2008. *Atherosclerosis* 196:643-649; Hernesniemi et al., 2009. *Eur Heart J* 30:2939-2946). SNP functionality in vitro is assayed and association with circulating IL-18 levels in a large sickle cell patient cohort is confirmed QTc is positively correlated with free levels heme and mortality in patients with sickle cell disease. Analyzing data submitted to publication (Indik et al., 2016. *PLoS One*) from two separate sickle cell cohorts (n=224 patients total), Kaplan-Meier survival curves from time of ECG acquisition stratified by the 90$^{th}$ percentile of QTc (480 ms) demonstrate significant separation (FIG. 7A). QTc was also significantly related to circulating free heme levels in plasma (FIG. 7B).

Figure 8:
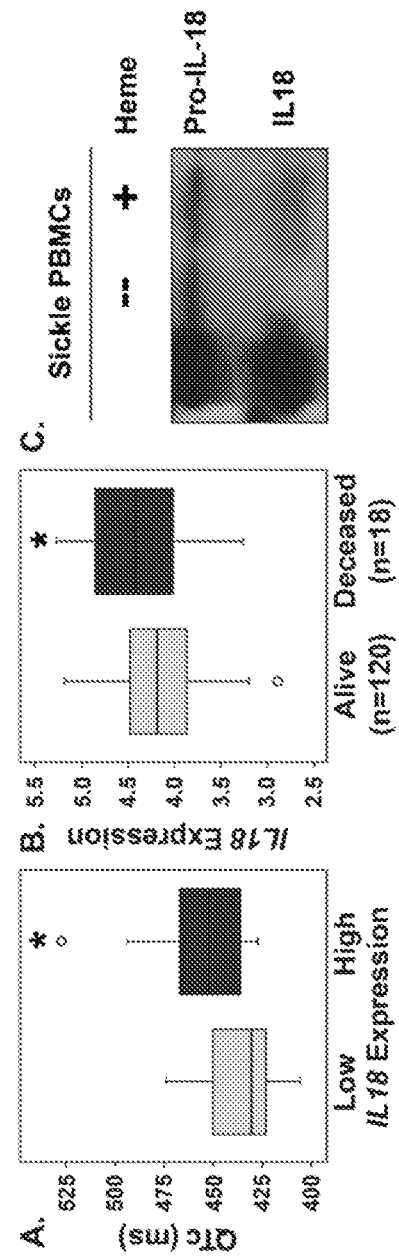
FIG. 8A-C show that IL18, associated with prolonged QTc and mortality, is induced by heme. A. High (vs low) PBMC IL18 expression levels are associated with longer QTc levels. n=28 total, P=0.047 B. Those patients who died also exhibited higher steady-state PBMC IL18 gene expression. P=0.02 C. Heme (100 uM, 16 h) administration in vitro to PBMCs isolated and cultured from patients with sickle cell disease induces IL-18 protein expression.

IL-18, associated with prolonged QTc and mortality, is induced by heme in PBMCs. Gene expression profiling from PBMCs from patients with sickle cell disease revealed significantly higher IL18 gene expression with levels of IL18 expression linked to both increased QTc intervals and sickle cell disease mortality (FIGS. 8A and 8B). Exposure of PBMCs isolated from a sickle cell disease patient to heme (16 h) induced IL-18 protein expression (FIG. 8C).

IL18 SNPs are associated with prolonged QTc, IL18 expression, and sudden cardiac death. Published data have reported an IL18 promoter SNP, rs187238, to be associated with sudden cardiac death (Hernesniemi et al., 2008, supra; Hernesniemi et al., 2009, supra). A candidate gene analysis (from available preliminary GWAS data of sickle cell disease patients) of regional SNPs near the IL18 gene revealed rs5744285 was one of the top SNPs associated with both IL18 gene expression (P=0.003, FIG. 8A) and prolonged QTc (P=0.012). Further analysis revealed that the CT (major alleles) haplotype of rs5744285 (T) and rs11214107 (C), containing both the IL18 promoter and 5' gene, showed a strong association and was associated with decreased IL18 expression (β=−0.29; P=0.002) and QTc (β=−0.019; P=0.0004) compared to other haplotypes. Furthermore, it was observed that rs5744285, an IL18 promoter region SNP, was associated with diastolic dysfunction in patients with sickle cell disease (50)

Heme-responsive IL18 promoter regions linked to increased expression are identified. Promoter regulatory elements (from the transcription start site, TSS, to −3000bp) of the IL18 promoter that are critical for its expression are evaluated by transfecting THP-1 cells [a promonocytic cell line available from the American Type Culture Collection (ATCC, Manassas, Va.)], cultured in RPMI 1640 medium containing 10% heat-inactivated fetal bovine serum, 10 h, 6-well plates, in triplicate) with full-length or serially-deleted (~50-300 bp spacing) reporter luciferase constructs containing promoter followed by exposure to vehicle and heme and quantification of IL18 firefly luciferase activity in lysates as previously reported (Ye et al., 2005. *Am J Respir Crit Care Med* 171:361-370; Wadgaonkar et al., 2005. *J Cell Biochem* 94:351-364). Heme concentration and duration of exposure are also be determined for optimal IL18 expression response; 100 uM of heme for 16 h is used as a positive control for response.

The contribution of select transcription factors to heme-responsive IL18 expression is identified. After identifying promoter fragments upregulated by heme and the minimal heme-responsive IL18 element, in silico analyses on TFs (FIG. 11) predicted to bind to consensus sequences on the IL18 promoter. Binding of these select TFs after heme exposure is confirmed using electrophoretic mobility shift assay (EMSA) and ChIP. One of these TFs, STAT3, is known to be induced by free heme (Liu et al., 2013. PLoS One 8:e71366). Another TF, BCL6 is an established transcriptional repressor of human and murine IL18 genes with known promoter binding sites (2686bp upstream of TSS). It is also evaluated how heme exposure may influence BCL6 and other TF binding to the IL18 promoter that contributes to IL18 reporter activation (Zhang et al., 2008. *FEBS Lett* 582:1802-1808). For example, BCL6 expression is reduced (siRNA) and the full length/deletion series of IL18 luciferase reporters or real time PCR and optimize conditions (time, siRNA concentration and siRNA sequence) is used for silencing IL18 prior to exposure to heme (0, 1, 2, 6 and 16 h). Cell lysates are harvested for RNA (real-time PCR) or lysates (luciferase activity) (each in triplicate). These studies allow one to identify whether these select TFs are involved in IL18 responses to increased heme.

Heme-responsive IL18 promoter region SNPs resulting in increased IL18 expression are evaluated. The influence of the six IL18 SNPs (listed in Table 1) on heme-induced IL18 expression is evaluated by introducing these SNPs into the IL-18 luciferase reporter by site-directed mutagenesis (SDM) and transfecting THP-1 cells. Responses to heme are evaluated as described for SNPs in other gene promoters (Ye et al., 2005. *Am J Respir Crit Care Med* 171:361-370). In companion experiments, the effects of IL18 promoter SNPs on BCL6 (and other select TFs) promoter binding is defined by EMSA assays.

Prioritized IL18 are then validated SNPs with circulating IL-18 levels in a large sickle patient cohort. Blood samples from WALK-PHaSST cohort (Gladwin et al., 2014. *PLoS One* 9:e99489) with 635 sickle cell patients recruited from across the US are used to measure plasma circulating IL-18 levels and genotype patients for the top SNPs validated above.

TABLE 3

IL18 promoter SNPs

| SNP ID (Position from TSS) | Minor Allele Frequency | | |
|---|---|---|---|
| | Global | AD | ED |
| rs187238 (−368) | 0.212 | 0.20 | 0.27 |
| rs5744226 (−725) | 0.0034 | 0.13 | 0.00 |
| rs5744225 (−814) | 0.0034 | 0.13 | 0.00 |
| rs360719 (−1529) | 0.2091 | 0.20 | 0.28 |
| rs5744223 (−1948) | 0.031 | 0.112 | 0.001 |
| rs11214107 (−6968) | 0.156 | 0.2 | 0.27 |

Example 3

Definition of Linkage of IL-18/IL-18R/Nox4 Signaling to Acute Downregulation of KCND2/KCND3 Function Leading to Delayed Repolarization and Chronic Development of Cardiac Fibrosis It is contemplated that IL-18/IL-18R signaling implicates Nox4 function in sickle heart arrhythmic response. In an acute setting, it is contemplated that IL-18-mediated Nox4 activation downregulates KCND2/KCND3 expression and associated $I_{to}$ activity which prolongs APD promoting VT; in a chronic setting, it is contemplated that IL-18 induces Nox4-mediated myocardial apoptosis and subsequent fibrosis resulting in pathologic electrophysiological remodeling enhancing VT vulnerability. Briefly, myocardial action potentials reflect the sequential activation and inactivation of inward depolarizing ($Na^+$, $Ca^{2+}$) and outward repolarizing ($K^+$) current-carrying ion channels. The $K^+$ channel function determines membrane potential and refractoriness of the myocardium. Data described herein shows exposure of sickle mice to circulating IL-18 to rapidly (within 5 min) increases Nox4 levels and reduce $I_{to}$ current in sickle cardiomyocytes. These observations are coupled with increased nitrotyrosine (ROS marker) levels and p38 MAPK activation (within 5 mins and sustained for 45 mins) in vivo. Reduced $I_{to}$ is also associated with IL-18-induced prolonged APD, promoting early after depolarizations (EADs) and reentry formation in sickle cell hearts. Several reports have shown direct Nox4 interactions with IL-18R as well as Nox4-medaited p38 MAPK activation in cardiomyocytes resulting in reduced KCND2/KCND3 mRNA expression (and $I_{to}$ current) (Li et al., 2012. *J Mol Cell Cardiol* 52:971-977; Zhou et al., 2008. *J Mol Cell Cardiol* 45:832-838; Zhou et al., 2006. *Circ Res* 98:1040-1047). Single cell voltage clamp and organ level optical mapping is used to evaluate the downstream effects of IL-18 and Nox4. Additionally, sustained (3 weeks) IL-18 inhibition was demonstrated using IL-18bp, which prevents binding of IL-18 to IL-18R, results in reduced myocardial apoptosis and fibrosis associated with reduced cardiac Nox4 and IL-18R expression levels. Based on these acute and chronic data, a mutant mouse with cardiac-specific Nox4 genetic depletion in a sickle cell mouse background is generated to functionally validate the role of cardiac Nox4 in sickle cell cardiomyopathy and inducible VT.

Sickle mice are characterized by prolonged APD. There is a paucity of information concerning cardiac pathobiology in sickle mice including the aberrant conduction abnormalities. Studies described in example 1 above of electrical mapping of sickle controls ("WT") and sickle mice ex vivo revealed longer APD, reduced longitudinal and transverse conduction velocity (CV) in sickle mice hearts, while no significant changes in rise-time of action potentials. These sickle murine myocardial characteristics are in complete agreement with published data in patients with sickle cell disease that demonstrate prolonged QTc, which has been associated with a risk of fatal VT and sudden cardiac death (Al-Zaiti et al., 2014. *Heart Lung* 43:527-533; Kenigsberg et al., 2007. *J Am Coll Cardiol* 49:1299-1305; Remme et al., 2013. *Cardiovasc Drugs Ther* 27:91-101; Sara et al., 2016. *J Electrocardiol* 49:87-93; Schwartz and Wolf, 1978. *Circulation* 57:1074-1077).

Figure 9:
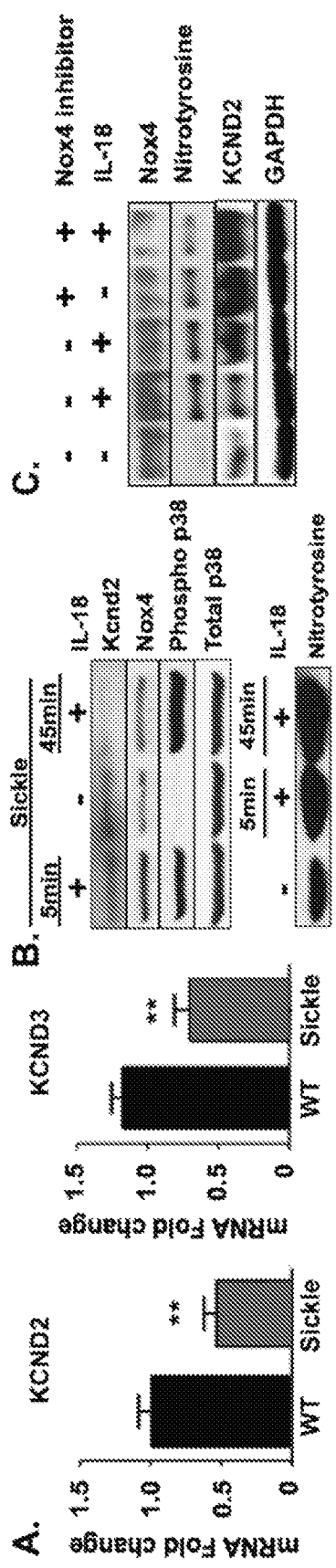
FIG. 9A-C shows acute IL-18-mediated cardiac Nox4 activation in sickle mice. A. KCND2/KCND3 mRNA are reduced in sickle compared to WT mice hearts. (n=6 mice each) B. Acutely, Nox4, p38, and nitrotyrosine are activated within 5 minutes of IL-18 administration to sickle mice (IJ, 5 ug/kg). C. Administration of a non-specific Nox inhibitor, diphenyleneiodonium, (DPI, 1.5 mM, IP) 3 h prior to IL-18 (1 ug/kg, U) administration, reduces both total Nox4 and nitrotyrosine levels and increases KCND2 levels in cardiac tissue in sickle mice.

IL-18 induces prolonged APD and short-lived VTs. Exogenous administration of IL-18 via the perfusate (20 ng/min) resulted in prolonged APD, reduced trends in CV, and increased rise time. After 20 min, IL-18 administration led to APD prolongation, atrioventricular block, and a slowed heart rate. Longer duration of perfusion of IL-18 led to the development of multiple PVCs and short-lived VTs (n=4/4 hearts). Analysis of action potentials revealed that PVCs were initiated before the previous action potential fully repolarized, indicating that prolonged APD under IL-18 resulted in EADs. These intact heart mapping data indicate that prolongation of APD and slowing CV in sickle cell hearts stem from electrophysiological remodeling that creates a vulnerable environment for the development to VT Acute IL-18 exposure mediates cardiac Nox4/p38 activation in sickle mice. Sickle mice have reduced KCND2/KCND3 RNA (FIG. 9A) and protein compared to sickle control ("WT") mice, linking to their prolonged APD. IL-18 exposure in vivo acutely induces cardiac Nox4, p38 activation, and nitrotyrosine levels (FIG. 9B). The acuity of the expression changes in Nox4 reflect IL-18 mediated post-translational rather than transcriptional modifications (reduced Nox4 degradation). Nitrotyrosine levels are considered a stable byproduct of the presence of peroxynitrite (ROS). Exposure of a non-specific Nox inhibitor, diphenyleneiodonium, (DPI), prior to IL-18 administration reduces both cardiac Nox4 and nitrotyrosine levels while increasing KCND2 levels (FIG. 9C).

Figure 10:
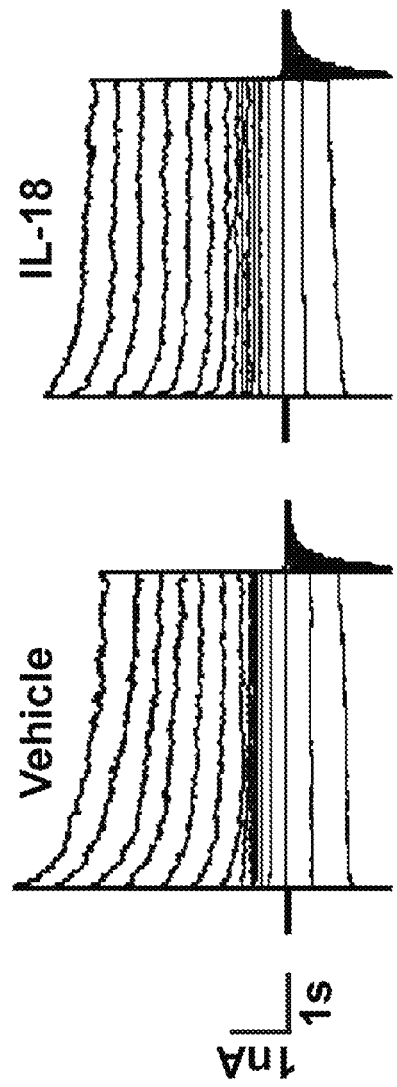
FIG. 10 shows the effect of IL-18 on Ito in sickle mouse myocytes.

IL-18 reduces $I_{to}$ in isolated sickle cardiomyocytes. Voltage clamp experiments were performed on fresh cardiomyocytes isolated from a sickle mouse exposed to IL-18 (FIG. 10). In 10 minutes, IL-18 markedly reduced $I_{to}$ (47% reduction), mostly derived from the reduction in rapid inactivation component.

IL-18 expression is associated with cardiac fibrosis and dysfunction. Evaluation of PBMC-derived gene expression profiling in sickle cell disease patients (n=34 patients) with and without evidence of myocardial fibrosis (evidenced by presence of late gadolinium enhancement or LGE) on cardiac MRI revealed 84 differentially expressed genes including high IL18 expression. IL-18 is a previously established pro-fibrotic inflammatory mediator whose circulating levels are associated with increased risk of sudden cardiac death (Hernesniemi et al., 2008; supra; Hernesniemi et al., 2009, supra; Blankenberg et al., 2002. *Circulation* 106:24-30). Histologic examination of three available human myocardial autopsy specimens from patients with sickle cell disease further supported these observations by demonstrating increased IL-18 staining in patients with a greater myocardial fibrosis burden. Increased circulating PBMC-derived IL18 expression from sickle cell disease patients associated with diastolic dysfunction as well as in sickle mouse LV tissue was observed (Desai et al., 2016. *Plos One*). These data show a positive association between increased circulating and myocardial IL-18 with the presence of myocardial fibrosis in sickle cell disease.

IL-18 inhibition reduces cardiac apoptosis and fibrosis, coupled with reduced IL-18R and Nox4 expression. IL-18bp is a naturally occurring protein that binds to IL-18 and efficiently prevents IL-18/IL-18R. Trials investigating the safety and efficacy of recombinant human IL-18bp (rhIL-18bp) have already been conducted in rheumatoid arthritis (O'Brien et al., 2014. *Mol Med* 20:221-229). Sustained IL-18 inhibition with IL-18bp in sickle mice resulted in reduced myocardial apoptosis and fibrosis, improved cardiac function (measured by change in filling pressures on echocardiography), and reduced cardiac IL-18R (β subunit) and Nox4 expression.

Determine role of IL-18R-mediated dysregulation of KCND2/KCND3 expression and ion channel function in sickle hearts and cardiomyocytes. It is contemplated that IL-18/IL-18R-mediated downregulation of KCND2/KCND3 expression and function prolongs APD via reducing $I_{to}$, which promotes EADs and reentry formation in sickle cell hearts. Single cell voltage clamp and organ level optical mapping is used to evaluate IL-18 effects on $I_{to}$ and electrophysiological remodeling. The contribution of KCND2/KCND3 and their respective channel (Kv4.2/Kv4.3) function is evaluated using patch clamp technique and in intact sickle mice hearts. Data from optical mapping indicates severe APD prolongation in the sickle LV; thus, cardiomyocyte cells are isolated from the murine LV (n=5/group) as has been previously reported (Hernesniemi et al., 2008, supra) from sickle control ("WT"), heterozygous, and sickle male mice (age 12-16 weeks) to evaluate gene dose effects.

Single cell voltage clamp of $I_{to}$ protocol: Baseline-isolated myocytes are first characterized electrically by patch-clamping using the whole-cell configuration in either current- (for AP recording) or voltage- (or AP)-clamp mode with an Axopathc-200B amplifier [for $I_{to}$ or L-type $Ca^{2+}$ current ($I_{Ca,L}$) recording] as previously reported (Hernesniemi et al., 2008, supra). To record pure $I_{to}$ and avoid $I_{Na}$ and $I_{CaL}$ from $I_{to}$ recordings, blockers for other channels are added to Tyrode's solution including the $I_{Ca,L}$ blocker, Cd3+ (0.3 mM), and Na+ current blocker tetrodotoxin (TTX, 10 μM). IL-18 effects-Based on data in a sickle mouse, $I_{to}$ is a major target by IL-18 and its reduction may explain the observed EADs. IL-18 is now be added to the solution and $I_{to}$ amplitude and inactivation kinetics is measured in replicates (n=5 mice each strain, males, 10-14 weeks of age). To verify the IL-18-mediated reduction of $I_{to}$ in sickle myocytes as a major mechanism underlying EADs, a dynamic clamp of calculated $I_{to}$, is applied by injecting simulated $I_{to}$ to the myocytes and investigating its efficacy in suppressing EADs. This approach avoids non-specific effects of pharmacological interventions. Furthermore, whether the amplitude of $I_{to}$ alone or its kinetics including activation and inactivation are also important for EAD formation in sickle LV cells is evaluated. A multi-function NiDAQmx card (NI PCIe-6321, National Instrument) is used to record $V_m$ and generate $I_{to}$ through a callback function every 10 μs sampling in real-time to the external I-command port in the AxoClamp 200B. All experiments will be carried out at 34-36° C.

Optical mapping of intact heart: Roles of $I_{to}$ in ex vivo intact heart are evaluated using optical mapping by interrupting $I_{to}$ pharmacologically with known activator (NS5806, (Calloe et al., 2010. *J Mol Cell Cardiol* 48:191-200; Lundby et al., 2010. *Br J Pharmacol* 160:2028-2044; Maleckar et al., 2014. *Europace* 16 Suppl 4:iv46-iv55)) and blocker (4-AP, (Fiset et al., 1997. *J Physiol (Loud)* 504:557-563)]. Specifically, all 3 strains (n=5 per group, males, 10-14 weeks of age) are anesthetized under isoflurane and hearts are excised from the chest and given retrograde perfusion through the aorta in a Langendorff perfusion system with Tyrode's solution as previously done (Brunner et al., 2008. *J Clin Invest* 118:2246-2259; Ziv et al., 2012. *Am JPhysiol Heart Circ Physiol* 302:H2321-2330; London et al., 2007. *J Physiol* 578:115-129). Blebbistatin (5 μmol/L) is perfused to reduce movement artifact. IL-18 is perfused 2~50 ng/min for optical mapping study. Hearts are stained with a voltage-sensitive dye, di-4-ANEPPS using 25 μL of stock solution (1 mg/ml of dimethyl sulfoxide, DMSO) delivered through a bubble trap, above the aortic cannula. ECGs is continuously monitored (PowerLab, ADlnstruments) and premature ventricular contractions (PVCs) or spontaneous VTs are monitored. The standard pacing protocol consists of 150 ms basic cycle length (BCL) and followed by multiple extra premature stimulations (S1S2, gradually decreased by 5 ms until loss of capture or induced VT). Fluorescence images from the LV free wall of the heart are captured using a CMOS camera (view 10×10 mm$^2$, sampling rate 2000 frames/s). APD, rise-time, and CV are analyzed with a custom-built software program using Interactive Data Language as previously described (Brunner et al., 2008. *J Clin Invest* 118: 2246-2259; Ziv et al., 2012. *Am J Physiol Heart Circ Physiol* 302:H2321-2330; London et al., 2007. *J Physiol* 578:115-129).

Therapeutic effect of IL-18 blockade by IL-18bp: The role of IL-18R is investigated by inhibiting IL-18R signaling using IL-18bp (15 μg/mouse/day) in mice 30 min [based on published kinetics/efficiency of IL-18bp for IL-18 (Kim et al., 2000. *Proc Natl Acad Sci US A* 97:1190-1195) prior to isolation of primary cardiomyocytes and in tact hearts. The dose and route of IL-18bp are based on data showing reduced cardiac IL-18R expression with inhibition of IL-18 signaling systemically. Patch clamping is then repeated using the whole-cell configuration as above (n=5) and ex vivo intact heart optical mapping (n=5) with and without IL-18 exposure in the perfusate (2-50 ng/min). Alternatively, siRNA targeting IL-18R systemically (prior to heart harvesting) is utilized.

The role of Nox4 and its interaction with IL-18R on KCND2/KCND3 expression and associated ion channel function in sickle cardiomyocytes and intact hearts. Data (Figure B )shows acute increases in cardiac Nox4 expression, ROS levels, and subsequent, p38 activation (within 5 mins which remains sustained for at least 45 mins) induced by circulating IL-18 in vivo. Separately published data have shown direct interactions between Nox4 with IL-18R as well as Nox4-mediated p38 MAPK activation [via peroxynitrite ROS increases (Pesse et al, 2005. *J Mol Cell Cardiol* 38:765-775)] in cardiomyocytes resulting in reduced KCND2/KCND3 mRNA expression (and $I_{to}$ current) (Li et al., 2006. *J Mol Cell Cardiol* 40:339-349; Zhou et al., 2012. *J Mol Cell Cardiol* 52:971-977; Zhou et al., 2008. *J Mol Cell Cardiol* 45:832-838; Zhou et al., 2006. *Circ Res* 98:1040-1047). It is contemplated that IL-18R-mediated Nox4 and downstream P38 activation acutely prolongs APD via reducing Ito, which promotes EADs and reentry formation in sickle cell hearts. Single cell voltage clamp and organ level optical mapping is used to evaluate electrophysiological remodeling due to interactions between IL-18R and Nox4/p38. Nox4 is inhibited using siRNA targeted to Nox4 in isolated cardiomyocytes. A time/dose response is performed for siRNA to determine adequate silencing in isolated cardiomyocytes and in mice before patch clamping as described above. Use of siRNA is monitored for each experiment to assess efficiency of knockdown with Western blot and real-time RT-PCR. At least two independent siRNA sequences targeting the same gene are used and results are compared to a scramble control. Rescue experiments utilizing siRNA-resistant forms of the genes of interest are used. The siRNAs is titered (<30 nM) to mitigate off-target effects observed at higher concentrations. Non-specific Nox inhibitors are also evaluated. As p38 activation is downstream of Nox4 based on published data (Zhou et al., 2006. *Circ Res* 98:1040-1047), a p38-specific inhibitor, SB203580 [based on previous use (Zhao et al., 2001. *Am J Physiol Heart Circ Physiol* 280:H1278-1285) (1 mg/kg intraperitoneal 24 h prior to isolation of myocytes for patch clamping and intact mapping) is used in acute experiments as previously demonstrated in reducing $I_{to}$ (Li et al., 2006. *J Mol Cell Cardiol* 40:339-349). Patch clamping is repeated using the whole-cell configuration and ex vivo heart perfusion system with and without IL-18 exposure (1 µg/mL) or infusion in the perfusate (2-50 ng/min), respectively. Five replicates per mouse strain are performed (males, 10-14 weeks of age) for each inhibitor (Nox4 siRNA, scramble RNA and SB203580).

The role of IL-18R/Nox4 signaling in the development of cardiac apoptosis and fibrosis in sickle mice. It was previously shown that sustained (3 weeks) IL-18 inhibition using IL-18bp, which prevents binding of IL-18 to IL-18R, results in reduced myocardial apoptosis and fibrosis associated with reduced cardiac Nox4 and IL-18R expression levels. It is hypothesized that sustained reduced cardiac Nox4 expression leads to decreased rates of myocardial apoptosis and fibrosis in sickle mice. Cardiac-specific Nox4 (cNox4$^{-/-}$) knockout mice (Kuroda et al., 2010. *Proc Natl Acad Sci USA* 107:15565-15570) are breed to generate a combination of cardiac Nox4 knockout mice in both a sickle and a sickle control ("WT") background. The combined mutant mice may display a vulnerable phenotype upon stressful stimuli. However, at baseline, cNox4$^{-/-}$ mice do not appear to have any obvious cardiovascular or systemic phenotype (Kuroda et al., 2010, supra) nox4 reduction may be beneficial for sickle mice. Alternative approaches including the use of 1) non-specific Nox inhibitors (FIG. 9C), 2) daily systemic siRNA in vivo, or P38 inhibitor (daily IP injections). Levels of myocardial apoptosis and fibrosis, and cardiac function are evaluated using echocardiography in these animals at 10-14 weeks and "WT", "WT"-cNox4$^{-/-}$, sickle, and sickle-cNox4$^{-/-}$ mice are compared at baseline. IL-18bp is then administered (1 µg/kg IP every other day for three weeks) and harvest mice as well as perform echo as described above. As separate experiments, IL-18 injections (25 µg/kg, IP based Yu et al., 2009. *Am J Physiol Heart Circ Physiol* 297:H76-85)] are administered daily for three weeks to these same strains of mice to determine levels of myocardial apoptosis, fibrosis, and function. These latter experiments provide information on the contribution of cardiac Nox4-specificty to IL-18 signaling in sickle cardiomyopathy including the potential for nox4 independent-influences. Ten replicates per strain (males, 10-14 weeks of age for phenotyping/harvesting tissue) are performed for all of the chronic experiments. A subset of these bred mice are subject to patch clamping and optical mapping. In some embodiments, antibodies are acquired from commercial sources and validated using several criteria: single band of the expected molecular weight by Western blot, use of positive and negative control cell lines and tissue sources (knockdown using siRNA or knockout murine tissues when available) and reproducibility between experimental runs and antibody lots.

Example 4

Therapies for Preventing Inducible VT in Preclinical Sickle Mice

Heme is an essential molecule for all cells and in addition to hemoglobin. Several hundred other proteins contain heme with diverse biological roles. In the cardiovascular system, heme plays a major role in gas exchange, mitochondrial energy production, antioxidant defense, and signal transduction (Sawicki et al., 2015. *J Am Heart Assoc* 4:e001138; Khechaduri et al., 2013. *J Am Coll Cardiol* 61:1884-1893). Despite the vital role of heme in the cardiovascular system, this molecule remains understudied outside of the erythropoietic system. Exposure to free heme potentially represents an initiating stimulus of the IL-18/Nox4 pathway, subsequent prolonged APD, and the development of sickle cardiomyopathy and inducible VT. Drugs that will either reduce circulating heme/hemolysis or IL-18 activity (directly or indirectly) that is specific to sickle cell disease are investigated. In particular, the effects of IL-18 antibody (IL-18ab) and the arrhythmic phenotype in a combined genetically-depleted cardiac Nox4$^{-/-}$/sickle transgenic mouse is tested. Hydroxyurea is tested for its ability to reduced hemolysis and improved mortality in sickle patients. Since hydroxyurea responses are variable (one third of patients do not respond), decitabine, an FDA-approved drug for myeloproliferative disorders which shows significant promise in reducing hemolysis and inducing Hemoglobin F in sickle cell patients, including those who do not respond to hydroxyurea is also tested.

Based on data (below) in sickle mice modeling a human electrophysiology (EP) study, the experimental model provides an excellent platform to screen for mechanisms and drug therapies in the arrhythmic-vulnerable sickle myocardium. While pacing-induced VT during an EP study in parallel conditions such as hypertrophic cardiomyopathy has shown mixed predictive and prognostic value (Behr et al., 2002. *Card Electrophysiol Rev* 6:482-486), the current observation in sickle cell mice may, nonetheless, still hold significant implications for an EP study on the vulnerability of sickle cardiomyopathy to spontaneous or inducible VT. Specifically, murine (and human) sickle cardiomyopathy is characterized by three conventional VT risk factors including fibrosis, diastolic dysfunction, and prolonged APD (Al-Zaiti et al., 2014. *Heart Lung* 43:527-533; Kenigsberg et al., 2007. *J Am Coll Cardiol* 49:1299-1305; Remme and Wilde, 2013. *Cardiovasc Drugs Ther* 27:91-101; Sara et al., 2016. *J Electrocardiol* 49:87-93; Schwartz and Wolf, 1978. *Circulation* 57:1074-1077) which contribute to its pathological electrophysiology remodeling, resembling the concept of "reduced repolarization reserve" (Roden, 1998. *Pacing Clin Electrophysiol* 21:1029-1034). This concept has been previously proposed as a general condition that promotes long QT-related arrhythmias such as EADs and Torsades de Pointes in particular with further stress. Both IL-18 administration or an EP study are therefore examples of these stressors and tools that can induce VT and validate this concept in sickle cell mice.

The same in vivo protocol used in (Rutledge et al., 2014. *J Am Coll Cardiol* 63:928-934) and the data below are used. Mice are anesthetized and intubated, before initiating an open-chest catheter protocol. Baseline ECG are acquired for 2 minutes (Millar); the data is stored and analyzed offline using the LabChart 7.1 (AD Instrument) software. Lead II recordings will be chosen for analyses. Programmed ventricular stimulation will be performed with a RV epicardial electrode connected to STG1008 stimulator (Multichannel systems, Reutlingen, Germany), where eight consecutive beats will be paced at 60 ms basic cycle length, followed by single, double and triple extra stimuli with incrementally deceasing cycle lengths between 20-55 ms, and inducible ventricular tachycardia will be defined as >3 consecutive ventricular beats. All experiments will be done with n=10 replicates for reproducibility and to meet power calculations.

Figure 12:
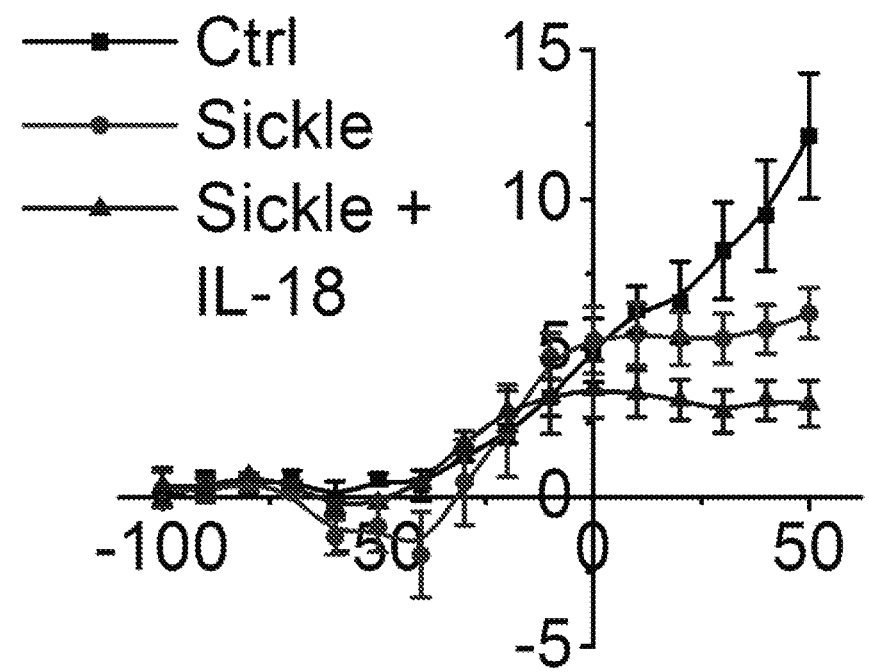
FIG. 12 shows I-V curves of peak I (to) in control, and sickle cell cardiomyocytes.

Sickle mice are vulnerable to pacing-induced VT. Sickle homozygous and sickle control ("WT") underwent an open-chest EP study (while intubated and anesthetized) in vivo where hearts of mice were stimulated with a catheter to induce rapid pacing (via either a programmatic or burst protocol). Unlike WT mice, nearly all but two sickle mice exhibited polymorphic VT (FIG. 12).

Evaluation of VT vulnerability in vivo in sickle mice after treatment with IL-18ab and with genetic depletion of cNox4$^{-/-}$ (combination mutant mouse). There are also early clinical trials of injectable IL-18 blocking antibodies (O'Brien et al., 2014. *Mol Med* 20:221-229) in type 2 diabetes. The primary advantage of an IL-18 neutralizing/blocking antibody (IL-18ab) is a longer elimination half-life that may allow monthly or quarterly administration. The efficacy of IL-18ab (5 mg/kg ip daily for three weeks vs vehicle, n=10 per strain, males, 10-14 weeks of age) is tested in the established inducible VT model in 3 mice strains (sickle control or "WT", heterozygote, homozygous). Heart tissue is evaluated for IL-18R Nox4, p38 activation levels, and fibrosis/apoptosis. Four more strains ("WT", combination of cNox4$^{-/-}$ in a "WT", sickle, combination of cNox4$^{-/-}$ in a sickle mouse) are assessed to determine VT vulnerability under Nox4 depletion (n=10 per strain, males, 10-14 weeks of age).

The role of hydroxyurea in preventing inducible VT in vivo. Hydroxyurea, first orally available drug approved by the FDA for sickle cell disease, is a potent inhibitor of ribonucleotide reductase which can induce hemoglobin F (HbF) levels in patients. While the response is variable and one third of patients do not respond, a large multicenter study of showed a marked decrease in the frequency of painful crises, episodes of acute chest syndrome, reduction in transfusion requirements and hospitalizations in adults with moderate to severe sickle cell disease (Steinberg et al., 1997. *Blood* 89:1078-1088; Charache et al., 1995. *N Engl J Med* 332:1317-1322) and was shown to have improved survival (Steinberg et al., 2003. *JAMA* 289:1645-1651). Sickle mice expressing high levels of HbF, because of gene transfer have also shown improvements in anemia and organ damage, showing that the inhibition of RBC sickling/hemolysis by HbF may be a major factor in long-term HU therapy. Unlike patients, however, long-term hydroxyurea administration in sickle mice does not improve hemolytic anemia (Nguyen et al., 2012. *Cardiovasc Res* 93:242-251) at baseline. Nonetheless, a recent study demonstrated acute beneficial effects of hydroxyurea in a tumor necrosis factor-α-induced vaso-occlusion model in sickle mice; short-term administration of hydroxyurea significantly altered leukocyte recruitment to the microvasculature coupled with prolonged animal survival (Xie et al., 2009. *Heart Rhythm* 6:1641-1649).

Hydroxyurea (n=10 per strain per dosing regimen, males, 10-14 weeks of age) is administered in two dosing schedules: 1) gavage with hydroxyurea or its vehicle (250 mg/kg orally as a one-time dose and prepared fresh, Sigma) 10 hours prior to EP testing 2) daily injection (50 mg/kg, IP) 5 days a week for 4 weeks prior to EP testing. The first dose tests whether there are any immediate beneficial effects that are brought about by stressing the heart with an EP study acutely. The second dose determines whether long-term hydroxyurea use may be able to prevent inducible VT in sickle mice despite the absence of change in heme levels (and in hemoglobin F/hemoglobin) via other yet unknown mechanisms including any effects on myocardial remodeling (e.g., fibrosis). Heart tissue is evaluated for levels of myocardial IL-18R Nox4, p38 activation, and myocardial fibrosis/apoptosis. A subset of these mice that are receiving hydroxyurea are administered IL-18 ex vivo to determine whether hydroxyurea will prevent IL-18 induced prolonged APD and VT (Lebensburger et al., 2010. *Haematologica* 95:1599-1603; Almeida et al.,. 2012. *Blood* 120:2879-2888).

The role of 5-Aza-2'-deoxycytidine (decitabine) in vivo. Decitabine, an analogue of 5-azacytidine and DNA hypomethylating agent FDA-approved for myelodysplastic syndromes, is known to induce HbF levels, mean γ-globin synthesis, and the fraction of F cells in patients with sickle cell disease (Yang et al., 2003. *Science* 302:1153; author reply 1153; Koshy et al., 2000. *Blood* 96:2379-2384; DeSimone et al., 2002. *Blood* 99:3905-3908). Moreover, decitabine use resulted in an increase in total hemoglobin levels of 2 g/dL while reticulocyte counts decreased, suggesting decreased hemolysis. In addition, 100% of sickle cell patients responded with an increase in HbF levels, including patients who had previously failed to respond to hydroxyurea with dose-limiting toxicity primarily being reversible neutropenia.

Based on previous administration and pharmacokinetic studies in mice (Terse et al., 2014. *Int J Toxicol* 33:75-85; Rivers et al., 2015. *Exp Hematol* 43:546-553 e541-543), decitabine is gavaged (n=10 per strain per dosing regimen) or its vehicle (1 mg/kg, Sigma) in two dosing schedules: 1) a single dose 1 day prior to EP testing 2) twice per week for 4 weeks prior to EP testing. The first dose tests whether there are any immediate effects that may be highly valuable in terms of its translational potential for patients who are experiencing an acute hemolytic crisis. The second dose determines whether sustained reductions in heme (and increases in hemoglobin F/hemoglobin) may be able to prevent inducible VT. Heart tissue is evaluated for levels of myocardial IL-18R Nox4, p38 activation, and myocardial fibrosis/apoptosis. A subset of these mice that are receiving decitabine are administered IL-18 ex vivo to determine whether decatibine will prevent IL-18 induced prolonged APD and VT (Lebensburger et al., 2010. Haematologica 95:1599-1603; Almeida et al., 2012. *Blood* 120:2879-2888).

Example 5

Effect of IL-8 on K$^+$ Currents

Methods

Patch clamp protocol of Ito: Cardiomyocytes were isolated by standard enzymatic techniques and patch-clamp recordings of Ito were performed with an Axopatch-200B amplifier (Molecular Devices, Sunnyvale, Calif.) as described previously (El Gebeily et al., Pharmacol. 2010 Mar. 10; 629(1-3):96-103). Bath solution was Tyrode solution (mmol/L): 140 NaCl; 5.4 KCl; 1.8 CaCl$_2$; 1 MgCl$_2$; 0.33, Na$_2$HPO$_4$; 10 HEPES, 5.5 glucose (pH adjusted to 7.4 with NaOH). Pipette solution is (mmol/L): 110 K$^+$-aspartate, 20 KCl, 8 NaCl, 1 MgCl$_2$, 1 CaCk$_2$, 10 BAPTA, 4 K2ATP and 10 HEPES (pH adjusted to 7.2 KOH). Whole-cell voltage-clamp recordings were made using the ruptured patch-clamp technique with a patch-clamp amplifier, Axopatch 200 B (Axon Instruments, Foster City, USA). Pipettes resistances was ~2 MΩ when filled with pipette solution. Series resistance in the whole-cell mode was compensated. Voltage-clamp currents were low-pass filtered at 1 kHz and digitized at 2 kHz. The total K+ current (Ipeak) was constructed from the current elicited by a series of 5 s test potentials at 10 mV increment from −110 mV to +50 mV from a holding potential of −80 mV at a frequency rate of 0.1 Hz. This voltage protocol was repeated with a 100-ms depolarizing step to −40 mV applied immediately before the 5 s test pulses to voltage inactive Ito. The data were recorded using pClamp 10.6 and analyzed with Clampfit (Axon Instruments, Foster City, USA). Current amplitudes were normalized to the cell capacitance and expressed as pA/pF. All experiments were carried out at room temperature (20-22° C.).

Results

Figure 11:
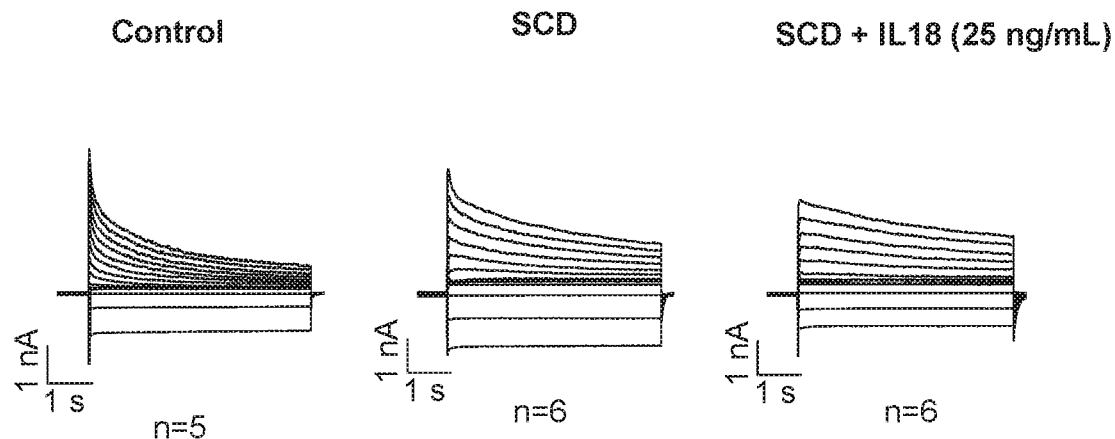
FIG. 11 shows the results of voltage clamp experiments in isolated murine cardiomyocytes.

Results are shown in FIGS. 11 and 12. FIG. 11 shows reduction of Ito in SCD, which can be further reduced by IL-18. IL-18 mostly abolished fast inactivating Ito. FIG. 10 shows the representative recordings of Ito (left) and current-voltage relationships (right) for cardiomyocytes isolated from WT, sickle mice, and sickle mice in the presence of IL-18. Ito was significantly reduced in sickle mice, which was further reduced by IL-18, in line with RT-PCR results of KCND2 and KCND3 PCR.

FIG. 12 shows Vm dependent plateau shape of Ito curves, due to slow activation of Ito. Therefore, Ito is not only reduced but its kinetics are also altered in SCD. FIG. 12 shows representative recordings of Ito from voltage clamped single myocytes isolated from a sickle mouse heart (left) and the peak current-voltage relationships (right) from WT (squares), sickle mice (circles), and sickle mice in the presence of IL-18 (triangles, 25 ng/mL). Ito was significantly reduced (12.1±2.1 in ctr vs. 6.1±0.8 pA/pF in sickle at 50 mV, p<0.01, n=6 cells) in line with RT-PCR data. IL-18 further reduced Ito in sickle group (3.1±0.8 pA/pF, p<0.01)

The functional consequence of KCND2 and KCND3 gene expression levels were verified with a patch clamp study of transient outward K+ current (Ito). Since KCND2 and KCND3 encode Kv4.2 and Kv4.3 underlie transient outward K$^+$ channels (Ito).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A method of detecting the presence of an IL-18 genotype in a sample from a subject, comprising: a) contacting a sample from a subject with at least two nucleic acid reagents that specifically hybridize to said IL-18 genotype that comprises a C/T at rs5744285, wherein said sample is a cardiac or blood sample, wherein said subject has sickle cell disease, sickle cell trait, hemolytic anemia, or increased levels of heme or IL-18 in circulation relative to a sample lacking said IL-18 genotype, wherein said nucleic acid reagent is selected from the group consisting of i) at least one nucleic acid probe that hybridizes to a C allele at rs5744285 and at least one nucleic acid probe that hybridizes to a T allele at rs5744285, and ii) at least one nucleic acid primer that hybridizes to a C allele at rs5744285 and at least one nucleic acid primer that hybridizes to a T allele at rs5744285; and b) detecting a hybrid resulting thereof.

2. The method of claim 1, further comprising the step of detecting one or more variants in said IL-18 gene, wherein said variants comprise a genotype selected from the group consisting of T/C or C/C at rs11214107; a haplotype of C/T at rs5744285 and T/C or C/C at rs11214107; a haplotype of T/C or C/C at rs11214107 and A/G or A/A at rs12796114; and a haplotype of T/C at rs5744285 and T/C or C/C at rs80008802.

3. The method of claim 1, wherein said nucleic acid reagent is detectably labelled, wherein said detecting comprises a detection technique selected from the group consisting of a hybridization assay, a sequencing assay, and an amplification assay.

4. A method of treating or preventing cardiac dysfunction and/or ventricular arrhythmia, comprising: a) detecting the presence of an IL-18 genotype in a sample from a subject, wherein said IL-18 genotype comprises a C/T at rs5744285, wherein said sample is a cardiac or blood sample, wherein said subject has sickle cell disease, sickle cell trait, hemolytic anemia, or increased levels of heme or IL-18 in circulation relative to a sample lacking said IL-18 genotype; and b) administering an anti-IL-18 treatment when said IL-18 genotype is present, wherein said anti-IL-18 treatment is selected from the group consisting of interleukin 18 binding protein (IL-18 bp), hydroxyurea and decitabine.

5. The method of claim 4, further comprising the step of detecting one or more variants in said IL-18 gene, wherein said variants comprise a genotype selected from the group consisting of T/C or C/C at rs11214107; a haplotype of C/T at rs5744285 and T/C or C/C at rs11214107; a haplotype of T/C or C/C at rs11214107 and A/G or A/A at rs12796114; and a haplotype of T/C at rs5744285 and T/C or C/C at rs80008802.

6. The method of claim 4, wherein said detecting comprises contacting a sample from the subject with a nucleic acid reagent that specifically hybridizes to an IL-18 gene, wherein said nucleic acid reagent is selected from the group consisting of i) at least one nucleic acid probe that hybridizes to a C allele at rs5744285 and at least one nucleic acid probe that hybridizes to a T allele at rs5744285, and ii) at least one nucleic acid primer that hybridizes to a C allele at rs5744285 and at least one nucleic acid primer that hybridizes to a T allele at rs5744285.

7. The method of claim 4,
wherein said nucleic acid reagent is detectably labelled,
wherein said detecting comprises a detection technique selected from the group consisting of a hybridization assay, a sequencing assay, and an amplification assay.

* * * * *